US008110352B2

(12) United States Patent
Roth et al.

(10) Patent No.: US 8,110,352 B2
(45) Date of Patent: Feb. 7, 2012

(54) METHOD OF DIAGNOSING AND TREATING CANCER USING B-CATENIN SPLICE VARIANTS

(75) Inventors: Mark J. Roth, Chevy Chase, MD (US); Konrad Huppi, Herndon, VA (US)

(73) Assignee: The United States of America as represented by the Secretary, Department of Health & Human Services, Washington, DC (US)

( * ) Notice: Subject to any disclaimer, the term of this patent is extended or adjusted under 35 U.S.C. 154(b) by 159 days.

(21) Appl. No.: 11/883,694

(22) PCT Filed: Feb. 10, 2006

(86) PCT No.: PCT/US2006/005032
§ 371 (c)(1),
(2), (4) Date: Apr. 10, 2008

(87) PCT Pub. No.: WO2006/086772
PCT Pub. Date: Aug. 17, 2006

(65) Prior Publication Data
US 2009/0111762 A1 Apr. 30, 2009

Related U.S. Application Data

(60) Provisional application No. 60/652,154, filed on Feb. 10, 2005, provisional application No. 60/667,084, filed on Mar. 30, 2005.

(51) Int. Cl.
*C12Q 1/68* (2006.01)
*G01N 33/574* (2006.01)
(52) U.S. Cl. ......................... 435/6.1; 435/7.21; 435/7.23
(58) Field of Classification Search .................. None
See application file for complete search history.

(56) References Cited

U.S. PATENT DOCUMENTS

2003/0064384 A1   4/2003   Hung et al.

FOREIGN PATENT DOCUMENTS

| WO | 98/42296 A3 | 10/1998 |
|----|-------------|---------|
| WO | WO-98/42296 | 10/1998 |
| WO | 03/051905   | 6/2003  |
| WO | 2004/005457 | 1/2004  |

OTHER PUBLICATIONS

Rimm et al. (American Journal of Pathology, 1999, 154(2): 325-329).*
Taber's Cyclopedic Medical Dictionary (1985, F.A. Davis Company, Philadelphia, p. 274.*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Boyd (The Basic Science of Oncology, 1992, McGraw-Hill, Inc., p. 379).*
Tockman et al. (Cancer Res., 1992, 52:2711s-2718s).*
Pritzker (Clinical Chemistry, 2002, 48:1147-1150).*
Kramer and Coen (Current Protocols in Molecular Biology 2001 15.1.1-15.1.14.).*
Roth et al., Genes, Chromosomes & Cancer, 44(4):423-428 (2005).
Roth et al., Cancer Detection and Prevention, 26(1), 2002.
Roth et al, Proceedings of the American Association for Cancer Research, 44:2285 (2003).
Nollet et al., Genomics, 32(3):413-424 (1996).
Jamieson et al., N. Engl. J. Med., 351(7):657 (2004).
Clarke, N. Engl. J. Med., 351(7):634 (2004).
Roth et al., 2003 Abstract American Association for Cancer Research Annual Meeting.
Roth et al., 2002 Abstract Cancer Detection and Prevention.
Roth, Mark J, et al.; "beta-catenin splice variants and downstream targets as markers for neoplastic progression of esophogeal cancer" Genes Chromosomes Cancer 44(4): 423-8 (Dec. 2005).
Roth, Mark J, et al.; "A study of B-catenin splice variants and associated downstream targets in neoplastic progression of squamous cell carcinoma of the esophagus (ESCC)" Proceedings of the AACR vol. 44, 2nd ed, p. 448, Abstract 2285 (Jul. 2003).
Roth, Mark J, et al.; "Proteomic analysis of beta-catenin during the neoplastic progression from precursor lesions to invasive squamous cell carcinoma of the esophagus" Proceedings of the AACR p. S-148; Abstract 352 (2002).
Nollet, Frank, et al.; "Genomic organization of the human beta-catenin gene (CTNNB1)" Genomics; 32(3): 413-24 (Mar. 15, 1996).
Jamison, CH, et al.; "Granulocyte-macrophage progenitors as candidate leukemic stem cells in blast-crisis CML" N Engl J Med; 351(7): 657-67 (Aug. 12, 2004).
Clarke, MF; "Chronic myelogenous leukemia—identifying the hydra's heads" N Engl J Med; 351(7): 634-6 (Aug. 12, 2004).
Pinto et al., Genes and Development, 17:1709-1713 (2003).
Y. Bian et al., American Journal of Clinical Pathology, 114(4):583-590 (2000).
Willert et al., Curr Opin Genet Dev. 8(1):95-102 (1998).
Kimura et al., Int. J. Cancer, 84(2):174-178 (1999).
Hurlstone et al., Nature, 425(6958):633-637 (2003).
Gat et al., Cell, 95:605-614 (1998).
Hu et al., Mol Pharmacol, 62:881-887 (2002).
Oro et al., Cell, 95:575-578 (1998).
Osterheld et al., Am J Clin Pathol, 117:451-456 (2002).
Roth et al., Cancer Research, 61:4098-4104 (2001).
Roth et al., Poster American Association for Cancer Research Meeting, Jul. 11-14, 2003.
Brabletz, T. et al. Nat Rev Cancer. Sep;5(9):744-9. 2005.
Radtke and Clevers. Science 307:1904-1909. 2005.
Reya and Clevers. Nature. 434:843-850. 2005.
van Es et al., Nature Cell Biology. 7:381-386. 2005.

* cited by examiner

*Primary Examiner* — Peter J Reddig
(74) *Attorney, Agent, or Firm* — Edwards Wildman Palmer LLP; Peter F. Corless; Christine C. O'Day

(57) ABSTRACT

The invention relates to method of diagnosing and treating cancer, in particular β-catenin related cancers. The invention further relates to methods of identifying CTNNB1 related cancer CTNNB1 therapeutics.

7 Claims, 14 Drawing Sheets

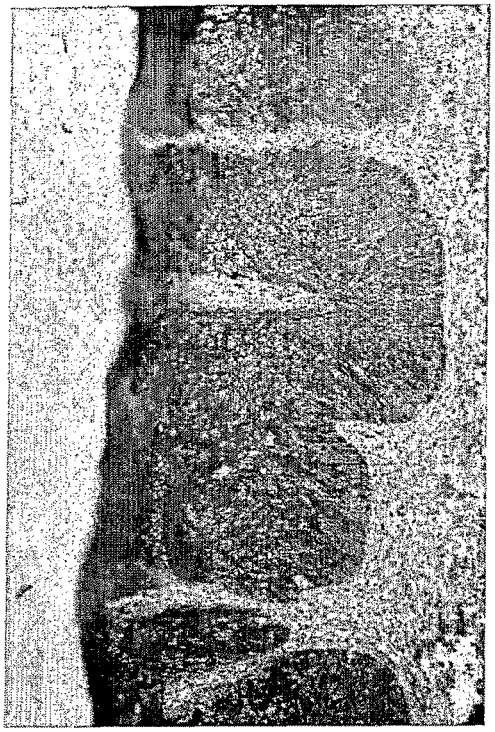
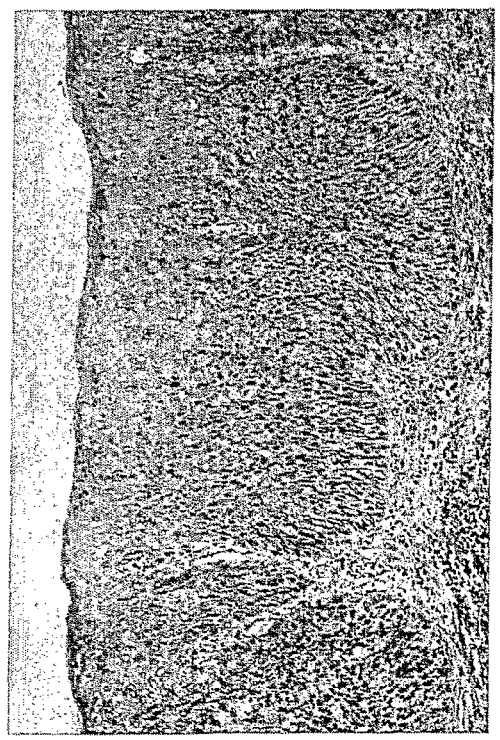
Figure 4

| Gene | Forward Primer (5' to 3') | Reverse Primer (5' to 3') |
|---|---|---|
| CTNNB1 complete cDNA | AGC CAC AAG ATT ACA AGA AAC (SEQ ID NO: 12) | AGG CTA GGG TTT GCT AAA TTC (SEQ ID NO: 13) |
| CTNNB1 16A isotype (exons 11-16) | GTT ATC AAG AGG ACT AAA TAC CA (SEQ ID NO: 8) | GAC AAT ACA GCT AAA TGA TGA T (SEQ ID NO: 9) |
| CTNNB1 16B isotype (exons 11-16) | GTT ATC AAG AGG ACT AAA TAC CA (SEQ ID NO: 10) | GTA TTG TTA CTC CTA AAG GAT GA (SEQ ID NO: 11) |
| c-MYC (exons 2 and 3) | GCC CCT GGT GCT CCA TGA (SEQ ID NO: 14) | ACC CTC TTG GCA GCA GGA TA (SEQ ID NO: 15) |
| p21 (Waf1) (exons 1 and 2) | ACA GCA GAG GAA GAC CAT GTG (SEQ ID NO: 16) | GGG CTT CCT CTT GGA GAA GAT (SEQ ID NO: 17) |
| 18s rRNA | TCAAGAACGAAAGTCGGAGG (SEQ ID NO: 18) | GGACATCTAAGGGCATCACA (SEQ ID NO: 19) |
| Beta-Actin | CCA CAC TGT GCC CAT CTA CG (SEQ ID NO: 20) | CAG CGG AAC CGC TCA TTG CCA ATG G (SEQ ID NO: 21) |

```
   1 cccacgcgtc cgggcagcag cgttggcccg gccccgggag cggagagcga ggggaggcgg
  61 agacggagga aggtctgagg agcagcttca gtccccgccg agccgccacc gcaggtcgag
 121 gacggtcgga ctcccgcggc gggaggagcc tgttcccctg agggtatttg aagtatacca
 181 tacaactgtt ttgaaaatcc agcgtggaca atggctactc aagctgattt gatggagttg
 241 gacatggcca tggaaccaga cagaaagcg gctgttagtc actggcagca acagtcttac
 301 ctggactctg gaatccattc tggtgccact accacagctc cttctctgag tggtaaaggc
 361 aatcctgagg aagaggatgt ggatacctcc caagtcctgt atgagtggga cagggatt
 421 tctcagtcct tcactcaaga acaagtagct gatattgatg gacagtatgc aatgactcga
 481 gctcagaggg tacgagctgc tatgttccct gagacattag atgagggcat gcagatccca
 541 tctacacagt ttgatgctgc tcatcccact aatgtccagc gtttggctga accatcacag
 601 atgctgaaac atgcagttgt aaacttgatt aactatcaag atgatgcaga acttgccaca
 661 cgtgcaatcc ctgaactgac aaaactgcta aatgacgagg accaggtggt ggttaataag
 721 gctgcagtta tggtccatca gctttctaaa aaggaagctt ccagacacgc tatcatgcgt
 781 tctcctcaga tggtgtctgc tattgtacgt accatgcaga atacaaatga tgtagaaaca
 841 gctcgttgta ccgctgggac cttgcataac ctttcccatc atcgtgaggg cttactggcc
 901 atctttaagt ctggaggcat tcctgccctg gtgaaaatgc ttggttcacc agtggattct
 961 gtgttgtttt atgccattac aactctccac aacctttat tacatcaaga aggagctaaa
1021 atggcagtgc gtttagctgg tgggctgcag aaaatggttg ccttgctcaa caaaacaaat
1081 gttaaattct tggctattac gacagactgc cttcaaattt tagcttatgg caaccaagaa
1141 agcaagctca tcatactggc tagtggtgga ccccaagctt tagtaaatat aatgaggacc
1201 tatacttacg aaaaactact gtggaccaca agcagagtgc tgaaggtgct atctgtctgc
1261 tctagtaata agccggctat tgtagaagct ggtgaatgc aagctttagg acttcacctg
1321 acagatccaa gtcaacgtct tgttcagaac tgtctttgga ctctcaggaa tctttcagat
1381 gctgcaacta aacaggaagg gatgaaggt ctccttggga ctcttgttca gcttctgggt
1441 tcagatgata taaatgtggt cacctgtgca gctgaattc tttctaacct cacttgcaat
1501 aattataaga acaagatgat ggtctgccaa gtgggtggta tagaggctct tgtgcgtact
1561 gtccttcggg ctggtgacag ggaagacatc actgagcctg ccatctgtgc tcttcgtcat
1621 ctgaccagcc gacaccaaga agcagagatg gcccagaatg cagttcgcct tcactatgga
1681 ctaccagttg tggttaagct cttacaccca ccatcccact ggcctctgat aaaggctact
1741 gttggattga ttcgaaatct tgcccttttgt cccgcaaatc atgcaccttt gcgtgagcag
1801 ggtgccattc cacgactagt tcagttgctt gttcgtgcac atcaggatac ccagcgccgt
1861 acgtccatgg gtgggacaca gcagcaattt gtggaggggg tccgcatgga agaaatagtt
1921 gaaggttgta ccggagccct tcacatccta gctcgggatg ttcacaaccg aattgttatc
1981 agaggactaa ataccattcc attgtttgtg cagctgcttt attctcccat tgaaaacatc
2041 caaagagtag ctgcaggggt cctctgtgaa cttgctcagg acaaggaagc tgcagaagct
2101 attgaagctg agggagccac agctcctctg acagagttac ttcactctag gaatgaaggt
2161 gtggcgacat atgcagctgc tgtttttgttc cgaatgtctg aggacaagcc acaagattac
2221 aagaaacggc tttcagttga gctgaccagc tctctcttca gaacagagcc aatggcttgg
2281 aatgagactg ctgatcttgg acttgatatt ggtgcccagg agaaccct tggatatcgc
2341 caggatgatc ctagctatcg ttcttttcac tctggtggat atggccagga tgccttgggt
2401 atggacccca tgatggaaca tgagatgggt ggccaccacc ctggtgctga ctatccagtt
2461 gatgggctgc cagatctggg gcatgccag gacctcatgg atgggctgcc tccaggtgac
2521 agcaatcagc tggcctggtt tgatactgac ctgtaaatca tccttaggt aagaagttt
2581 aaaaagccag tttgggtaaa atacttttac tctgcctaca gaacttcaga aagacttggt
2641 tggtagggtg ggagtggttt aggctatttg taaatctgcc acaaaaacag gtatatactt
2701 tgaaaggaga tgtcttggaa cattggaatg ttctcagatt tctggttgtt atgtgatcat
2761 gtgtggaagt tattaacttt aatgtttttt gccacagctt ttgcaactta atactcaaat
2821 gagtaacatt tgctgtttta aacattaata gcagcctttc tctctttata cagctgtatt
2881 gtctgaactt gcattgtgat tggcctgtag agttgctgag agggctcgag gggtgggctg
2941 gtatctcaga aagtgcctga cacactaacc aagctgagtt tcctatggga acaattgaag
```

Figure 9 (cont.)

```
3001 taaactttt  gttctggtcc  tttttggtcg  aggagtaaca  atacaaatgg  attttgggag
3061 tgactcaaga  agtgaagaat  gcacaagaat  ggatcacaag  atggaattta  gcaaaccta
3121 gccttgcttg  ttaaaatttt  ttttttttt   ttttaagaat  atctgtaatg  gtactgactt
3181 tgcttgcttt  gaagtagctc  ttttttttt   tttttttt    tttttttgc   agtaactgtt
3241 ttttaagtct  ctcgtagtgt  taagttatag  tgaatactgc  tacagcaatt  tctaattttt
3301 aagaattgag  taatggtgta  gaacactaat  taattcataa  tcactctaat  taattgtaat
3361 ctgaataaag  tgtaacaatt  gtgtagcctt  tttgtataaa  atagacaaat  agaaaatggt
3421 ccaattagtt  tcctttttaa  tatgcttaaa  ataagcaggt  ggatctattt  catgttttg
3481 atcaaaaact  atttgggata  tgtatgggta  gggtaaatca  gtaagaggtg  ttatttggaa
3541 ccttgttttg  gacagtttac  cagttgcctt  ttatcccaaa  gttgttgtaa  cctgctgtga
3601 tacgatgctt  caagagaaaa  tgcggttata  aaaatggtt   cagaattaaa  cttttaattc
3661 attcaaaaaa  aaaaaaaaaa  aaaaaaaaaa  aaaaaaa
```

Figure 10

"MATQADLMELDMAMEPDRKAAVSHWQQQSYLDSGIHSGATTTAP
SLSGKGNPEEEDVDTSQVLYEWEQGFSQSFTQEQVADIDGQYAMTRAQRVRAAMFPET
LDEGMQIPSTQFDAAHPTNVQRLAEPSQMLKHAVVNLINYQDDAELATRAIPELTKLL
NDEDQVVVNKAAVMVHQLSKKEASRHAIMRSPQMVSAIVRTMQNTNDVETARCTAGTL
HNLSHHREGLLAIFKSGGIPALVKMLGSPVDSVLFYAITTLHNLLLHQEGAKMAVRLA
GGLQKMVALLNKTNVKFLAITTDCLQILAYGNQESKLIILASGGPQALVNIMRTYTYE
KLLWTTSRVLKVLSVCSSNKPAIVEAGGMQALGLHLTDPSQRLVQNCLWTLRNLSDAA
TKQEGMEGLLGTLVQLLGSDDINVVTCAAGILSNLTCNNYKNKMMVCQVGGIEALVRT
VLRAGDREDITEPAICALRHLTSRHQEAEMAQNAVRLHYGLPVVVKLLHPPSHWPLIK
ATVGLIRNLALCPANHAPLREQGAIPRLVQLLVRAHQDTQRRTSMGGTQQQFVEGVRM
EEIVEGCTGALHILARDVHNRIVIRGLNTIPLFVQLLYSPIENIQRVAAGVLCELAQD
KEAAEAIEAEGATAPLTELLHSRNEGVATYAAAVLFRMSEDKPQDYKKRLSVELTSSL
FRTEPMAWNETADLGLDIGAQGEPLGYRQDDPSYRSFHSGGYGQDALGMDPMMEHEMG
GHHPGADYPVDGLPDLGHAQDLMDGLPPGDSNQLAWFDTDL"

METHOD OF DIAGNOSING AND TREATING CANCER USING B-CATENIN SPLICE VARIANTS

RELATED PATENT APPLICATIONS

This patent application claims priority to provisional patent application Ser. No. 60/652,154 filed Feb. 10, 2005, and provisional patent application Ser. No. 60/667,084 filed Mar. 30, 2005, the contents of which are hereby incorporated by reference in their entirety. This application is the national stage filing under 35 U.S.C. 371 of PCT/US2006/005032.

GOVERNMENT SUPPORT

This work described herein was supported by the National Institutes of Health as part of the intramural research program through projects OH95-C-N027 and OH95-C-N026.

BACKGROUND

Cancer is a significant health problem throughout the world. Although advances have been made in its detection and therapy, current methods for the prevention and treatment are less than optimal. The course of treatment for particular types of cancer is often selected based on a variety of prognostic parameters, including an analysis of specific tumor markers. However, it remains difficult to evaluate pre-neoplastic and peri-neoplastic cells as well as the metastatic potential of a cancer. The high mortality observed in cancer patients indicates that improvements are needed in the diagnosis and management of the disease.

Particularly, in the case of certain tumor types, such as adenocarcinomas and squamous cell carcinomas, the improper activation of signaling cascade involving the β-catenin gene (CTNNB1) is an event in the neoplastic transformation and progression of some cells. However, for many of these CTNNB1 related cancers, there is no reliable method of early detection, diagnosis, prognosis, or treatment.

Current methods for early detection, diagnosis, prognosis, and treatment of CTNNB1 related cancers fail to satisfactorily reduce the morbidity associated with these diseases. There is a need in the art for reliable, accurate, and safe methods for early detection, diagnosis, prognosis, and treatment of CTNNB1 related diseases.

BRIEF SUMMARY

In one aspect, the invention provides a method of diagnosing, predicting, or prognostically or therapeutically evaluating a β-catenin gene (CTNNB1) related cancer or preoplastic lesion in a subject. CTNNB1-related cancers include those associated with CTNNB1 expression per se as well as the expression of other genes associated with the signaling pathway containing CTNNB1. The method comprises determining one or more proportions, levels, or the cellular localization of transcripts or proteins associated with CTNNB1-related cancers or preneoplastic lesions in a cell or cells from the subject; comparing the proportion, level, or cellular localization of these transcripts or proteins, to a standard proportion, level, or the cellular localization of these transcripts or protein; and correlating a modulated proportion, level, or the cellular localization of these transcripts or proteins in the cell from the subject to provide information which may have prognostic, diagnostic and/or therapeutic significance for the subject.

The proportion, level, or cellular localization of transcripts or proteins associated with CTNNB1-related cancers may include the proportion of 16A transcript to 16B transcript, the proportion of cMYC transcript to WAF1 transcript, the level of 16A transcript, the level of 16B transcript, the level of cMYC transcript, the level of WAF1 transcript, the proportion of cMYC protein to WAF1 protein, the proportion of CTNNB1 protein to one or more of the levels of 16A, 16B, cMYC or WAF1 transcripts, the level of cMYC protein, the level of WAF1 protein, the level of overall transcription activity, or the cellular localization of the CTNNB1 protein.

In one preferred embodiment, the invention provides methods and compositions that may be used as a diagnostic, prognostic, monitoring and screening tool using two CTNNB1 transcripts, 16A and 16B, present in histologically normal appearing esophageal squamous cells, squamous dysplasia, and invasive ESCC cells.

According to one embodiment, a decrease in the proportion of 16A transcript to 16B transcript indicates that the subject may have a CTNNB1 related cancer, preneoplastic lesion, or be at increased risk for developing cancer. According to a related embodiment, an increase in the proportion of cMYC transcript to WAF1 transcript indicates that the subject may have a CTNNB1 related cancer, a preneoplastic lesion, or at increased risk for developing cancer or preneoplastic disease.

According to another related embodiment, a decrease in the level of the 16A transcript or a decrease in the WAF1 transcript indicates that the subject may have a CTNNB1 related cancer, or at increased risk for developing cancer or preneoplastic disease.

According to yet another related embodiment, an increase in one or more of the levels of 16B transcript, cMYC transcript or the level of overall transcription activity indicates that the subject may have a CTNNB1 related cancer, or at increased risk for developing cancer or preneoplastic disease.

According to one embodiment, a standard proportion, level, or the cellular localization of a CTNNB1-related transcript or protein is the corresponding proportion, level, or the cellular localization of the same CTNNB1-related transcript or protein in a reference cell or population of cells.

In one embodiment, a reference cell is one or more of the following, cells from the subject, cultured cells, cultured cells from the subject, or cells from the subject pre-treatment.

In another aspect, the invention presents a method to assess whether a subject who has cancer, preneoplastic disease related to CTNNB1, or is at increased risk for cancer or preneoplastic disease related to CTNNB1 is likely to exhibit a favorable clinical response to a treatment or clinical intervention. The method comprises, determining one or more proportion, level, or cellular localization of a CTNNB1-related cancer transcript or protein as described above in a cancer cell or a surrogate cell from a subject; comparing the proportion, level, or cellular localization of the transcript or protein to a standard proportion, level, or cellular localization of the transcript or protein; and correlating a modulated proportion, level, or cellular localization of the transcript or protein in the cancer cell or surrogate cell to determine if the subject is likely to have a favorable clinical response to treatment or related clinical intervention.

According to certain embodiments, the treatment includes, for example, surgery, focal therapy (e.g., mucosectomy, argon plasma coagulator, cryotherapy), selenium fortification, celecoxib, chemoradiation therapy, chemotherapy, including, but not limited to, fluorouracil (5-FU), cisplatin, vinblastine, paclitaxel, depsipeptides, flavopiridol, melphalan, and decitabine.

According to one aspect, the cancer cell or surrogate cell may be one or more of a preneoplastic squamous epithelium, a squamous dysplasia, squamous cell carcinoma in-situ, an invasive esophageal squamous cell carcinoma, or any histological or cytological stage in-between.

In one embodiment, the cancer or preneoplastic disease is one or more of esophageal squamous cell carcinoma, gastrointestinal or esophageal adenocarcinoma, gastrointestinal or esophageal dysplasia, gastrointestinal or esophageal metaplasia, Barrett's intestinal tissue, pre-cancerous conditions in histologically normal appearing esophageal squamous mucosa, neoplasias and neoplasia precursor lesions of the cervix, lung, head, and neck.

In one embodiment, a decrease in the proportion of 16A transcript to 16B transcript indicates that the subject may have a cancer, preneoplastic lesion, or be at increased risk for developing cancer. In a related embodiment, an increase in the proportion of cMYC transcript to WAF1 transcript indicates that the subject may have cancer, a preneoplastic lesion, or is at increased risk for developing cancer or preneoplastic disease. In another related embodiment, a decrease in the level of the 16A transcript or in the WAF1 transcript indicates that the subject may have cancer, or at increased risk for developing cancer or preneoplastic disease. In yet another related embodiment, an increase in one or more of the levels of 16B transcript, cMYC transcript or the level of overall transcription activity indicates that the subject may have cancer, or at increased risk for developing cancer or preneoplastic disease.

According to another aspect, a method of identifying a tumor that responds to a CTNNB1 related directed therapy is present. The method comprises obtaining a tumor cell sample; determining one or more of the proportions, levels, or immunolocalizations described above in the tumor cell sample; comparing the proportion, level, or cellular localization in the tumor cell sample to a standard proportion, level, or cellular localization after treatment with a potential CTNNB1 related cancer treatment; and correlating a modulation in the proportion, level, or activity in the sample following treatment with the potential CTNNB1 related cancer treatment to determine if the tumor is likely to have a favorable clinical response to treatment with CTNNB1 related cancer treatment.

In one embodiment, the β-catenin gene (CTNNB1) related cancer is one or more of esophageal squamous cell carcinoma, gastrointestinal or esophageal adenocarcinoma, gastrointestinal or esophageal dysplasia, gastrointestinal or esophageal metaplasia, Barrett's intestinal tissue, pre-cancerous conditions in histologically normal appearing esophageal squamous mucosa, neoplasias and neoplasia precursor lesions of the cervix, lung, head, and neck.

In one embodiment, a decrease in the proportion of 16A transcript to 16B transcript indicates that the tumor may respond to a CTNNB1 related therapy. In a related embodiment, an increase in the proportion of cMYC transcript to WAF1 transcript indicates that the tumor may respond to a CTNNB1 related therapy. In another related embodiment, a decrease in the level of the 16A transcript or in the WAF1 transcript indicates that the tumor may respond to a CTNNB1 related therapy. In yet another related embodiment, an increase in one or more of the levels of 16B transcript, cMYC transcript or the level of overall transcription activity indicates that the tumor may respond to a CTNNB1 related therapy.

According to another aspect, the invention provides a method of selecting a subject with cancer, preneoplasia, or at increased cancer risk, for treatment with a molecule or composition directly or indirectly targeting CTNNB1. The method comprises determining the pre-treatment level of one or more of the above described proportions, levels, cellular localization in a cancer cell from the subject; administering a CTNNB1 therapeutically effective amount of CTNNB1 related cancer treatment to the subject; and determining the post-treatment level of one or more of the proportions, levels, cellular localizations, or activities in the tumor or target tissue after an initial period of treatment with the CTNNB1 related cancer treatment, wherein a modulation in the proportion, level, cellular localization or activity in the cancer cell or target tissue following treatment with CTNNB1 related cancer treatment is an indication that the lesion/patient is likely to have a favorable clinical response to treatment with CTNNB1 related cancer treatment.

In one embodiment, the initial period of treatment is the time required to achieve a steady-state plasma or cellular concentration of the CTNNB1 related cancer treatment.

In one embodiment, a decrease in the proportion of 16A transcript to 16B transcript indicates that the subject may respond favorably to a CTNNB1 related cancer treatment. In related embodiment, an increase in the proportion of cMYC transcript to WAF1 transcript indicates that the subject may respond favorably to a CTNNB1 related cancer treatment. In another related embodiment, a decrease in the level of the 16A transcript or in the WAF1 transcript indicates that the subject may respond favorably to a CTNNB1 related cancer treatment. In yet another related embodiment, an increase in one or more of the levels of 16B transcript, cMYC transcript or the level of overall transcription activity indicates that the subject may respond favorably to a CTNNB1 related cancer treatment.

In one embodiment, the method further comprises comparing one or more of the pre-treatment or post-treatment proportions, levels, or cellular localizations of the CTNNB1-related transcript(s) or protein(s) to a standard proportion, level, or cellular localization of the CTNNB1-related transcript(s) or protein(s).

In another aspect, the invention provides a method of treating a subject with a CTNNB1-related cancer. The method comprise determining the pre-treatment level of one or more of the above described proportions, levels, or cellular localizations, in a cancer cell from the subject and administering a CTNNB1 therapeutically effective amount of CTNNB1 related cancer treatment to the subject if one or more of the proportions, levels, or cellular localization indicates that treatment with a CTNNB1 related cancer treatment will be efficacious.

In one embodiment, the initial period of treatment is the time required to achieve a steady-state plasma or cellular concentration of the CTNNB1 related cancer treatment.

In another embodiment, the method further comprises the administration of an additional CTNNB1 therapeutic agent (anticancer, chemopreventive agent, anti-inflammatory) or treatment modality (e.g. esophagectomy, mucosectomy, radiation therapy).

In one aspect, a method of monitoring the progress of a subject being treated with CTNNB1 directed therapy is provided and comprises determining the pre-treatment level of one or more of the above described proportions, levels, or cellular localization, in a cancer cell from the subject; administering a CTNNB1 therapeutically effective amount of CTNNB1 related cancer treatment to the subject; and determining the level of one or more of the proportions, levels, or cellular localization in the tumor after an initial period of treatment with the CTNNB1 related cancer treatment, wherein a modulation of the proportion, level, cellular localization or activity in the cancer cell following administration of a CTNNB1 related cancer treatment is an indication that the cancer treatment is efficacious.

In one embodiment, the method further comprises administering a second CTNNB1 therapeutically effective amount of CTNNB1 related cancer treatment to the subject; and determining the level of one or more of the proportions, levels, or cellular localization in the tumor after a second period of treatment with the CTNNB1 related cancer treatment.

Another aspect provides a kit for determining a response to a CTNNB1-directed therapy in a subject comprising at least two reagents that determine one or more of the following in a cancer cell: the proportion of 16A transcript to 16B transcript, the proportion of cMYC transcript to WAF1 transcript, the level of 16A transcript, the level of 16B transcript, the level of cMYC transcript, the level of WAF1 transcript, the proportion of cMYC protein to WAF1 protein, the proportion of CTNNB1 protein to the level of 16A, 16B, cMYC or WAF1 transcripts, the level of cMYC protein, the level of WAF1 protein, the level of overall transcription activity, or the cellular localization of the CTNNB1 protein.

In one embodiment, the reagents are selected from one or more of a primer, polymerase, antibody, buffer, or label.

In another aspect, a composition comprising a container including CTNNB1 related cancer treatment compound or composition and a label or package insert with instructions for determining one or more of the proportions, levels, or cellular localization described above and comparing the proportion, level, or activity to a standard proportion, level, or activity, wherein if a modulated proportion, level, or activity in the cancer cell is found relative to the standard proportion, level, or cellular localization, administration of the CTNNB1 related cancer treatment compound to the subject.

In another aspect, a method of identifying a CTNNB1 related cancer therapeutic comprises treating a cancer cell with a test composition; determining one or more of the above described proportions, levels or cellular localization in the cancer cell; comparing the proportion, level, or cellular localization to a standard proportion, level, or cellular localization; and correlating a modulated proportion, level, or cellular localization in the cancer cell to determine if the test composition is likely to have clinical efficacy. For purposes of this application clinical efficacy is used to refer to efficacy as measured in a clinical setting and/or efficacy as measured in the context of R&D efforts to identify candidate compounds for further clinical investigation.

In one embodiment, an increase in the proportion of 16A transcript to 16B transcript indicates that the test composition is likely to have clinical efficacy. In a related embodiment, a decrease in the proportion of cMYC transcript to WAF1 transcript indicates that the test composition is likely to have clinical efficacy. In another related embodiment, an increase in the level of the 16A transcript or in the WAF1 transcript indicates that the test composition is likely to have clinical efficacy. In yet another related embodiment, a decrease in one or more of the levels of 16B transcript, cMYC transcript or the level of overall transcription activity indicates that the test composition is likely to have clinical efficacy.

In one aspect, the invention provides a method of diagnosing or predicting the presence of a β-catenin gene (CTNNB1) related cancer in a subject. The method comprises determining one or more proportions, levels, or the cellular localization of the CTNNB1-related transcript(s) in a cell or cells from the subject; comparing the proportion, level, or the cellular localization of the CTNNB1-related transcript(s), to a standard proportion, level, or the cellular localization; correlating a modulated proportion, level, or cellular localization in the cell from the to make a determination that the cancer is likely a CTNNB1 related cancer; and histologically determining the pathological stage of the cells.

In one aspect, the invention provides methods of treating a subject suffering from or susceptible to a β-catenin gene (CTNNB1) related disease comprising administering to a subject in need thereof an RNAi inducing entity.

In one embodiment, the RNAi inducing entity is an RNAi construct.

In another embodiment, the RNAi inducing entity is a small-interfering RNA (siRNA).
wherein the siRNA is 19-30 base pairs long. In a related embodiment, the RNAi construct is an expression vector having a coding sequence that is transcribed to produce one or more transcriptional products that produce siRNA in the treated cells. In another related embodiment, the RNAi construct is a hairpin RNA which is processed to an siRNA in the treated cells.
wherein the RNAi construct attenuates one or more target genes selected from the β-catenin gene (CTNNB1).

According to certain embodiments, the RNAi construct attenuates expression of a gene resulting in reducing proliferation.

In one embodiment, the RNAi construct is an expression vector having a coding sequence that is transcribed to produce one or more transcriptional products that produce siRNA in the treated cells.

Methods of the invention may further comprise administering an additional therapeutic agent to the subject.

In one embodiment, the siRNA has a sequence corresponding one or more of TATGGGAACAATTGAAGTAAA (16A-1) (SEQ ID NO.: 1), CAGAAAGTGCCTGACACACTA (16A-2) (SEQ ID NO.:2), CTCGGGATGTTCACAAC-CGAA (16A+16B-1) (SEQ ID NO.:3), ATGGGTAGGG-TAAATCAGTAA (16A+16B-2) (SEQ ID NO.:4) or fragments or variants of any one of SEQ ID NO.: 1, SEQ ID NO.:2, SEQ ID NO.: 3 or SEQ ID NO. 4.

In a related embodiment, the siRNA is at least about 80% identical to the nucleotide sequence identified by SEQ ID NO.: 5 or fragments or variants thereof. In another related embodiment, the siRNA is at least about 90% identical to the nucleotide sequence identified by SEQ ID NO.: 5 or fragments or variants thereof. In a further related embodiment, the siRNA is at least about 99.9% identical to the nucleotide sequence identified by SEQ ID NO.: 5 or fragments or variants thereof.

In one aspect, the invention provides, a method of treating a subject suffering from or susceptible to a β-catenin gene (CTNNB1) related cancer comprising administering to a subject a compound comprising a double stranded RNA comprising at least a portion of a CTNNB1 nucleic acid sequence, wherein the administering is sufficient to treat or prevent a CTNNB1 related cancer in the subject.

In one embodiment, the double stranded RNA is processed into small interfering RNAs (siRNAs) 19 to 25 nucleotides in length.

In another aspect, the invention provides, a method of treating a subject suffering from or susceptible to a β-catenin gene (CTNNB1) related cancer comprising administering to a subject a single-stranded small interfering RNA molecule (ss-siRNA), wherein the sequence of the ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo, the ss-siRNA being administered in an amount sufficient for degradation of the target mRNA to occur, thereby activating target-specific RNAi in the organism.

In one embodiment, the target sequence is CTNNB1.

In another embodiment, degradation of the target mRNA is such that the protein specified by the target mRNA is decreased by at least 10%.

According to one embodiment, the siRNA is 19-30 base pairs long.

In another embodiment, the si RNA attenuates one or more target genes selected from the β-catenin gene (CTNNB1).

In one embodiment, the ss-siRNA is administered by inhalation or intranasally.

In one aspect, the invention provides, a composition comprising one or more RNAi constructs formulated for administration to a subject and operative to attenuate one or more target genes selected from the β-catenin gene (CTNNB1).

In one embodiment, the composition is administered as an aerosol. In a related embodiment, the composition is administered intravenously.
wherein the composition is formulated in a delivery agent comprising a delivery enhancing moiety to enhance delivery to a cell of interest.

In another related embodiment, the delivery-enhancing moiety comprises an antibody, antibody fragment, or ligand that specifically binds to a molecule expressed by the cell of interest.

In one embodiment, the RNAi construct is 19-30 base pairs long.

According to certain embodiment, the RNAi construct is an expression vector having a coding sequence that is transcribed to produce one or more transcriptional products that produce siRNA in the treated cells.

In one embodiment, the RNAi construct is a hairpin RNA which is processed to an siRNA in the treated cells.

In another embodiment, the RNAi construct is formulated as supramolecular complexes including a multi-dimensional polymer network.

In particular embodiments, the RNAi construct is encapsulated or associated with liposomes.

According to one embodiment, the liposomes are cationic liposomes formed from cationic vesicle-forming lipids. In a related embodiment, the liposomes have an average diameter of less than about 200 nm.

According to one embodiment, wherein the subject is a mammal, e.g., a human, a primate, a dog, a cat, a cow, a pig, or a horse.

In one embodiment, the RNAi construct is an expression vector having a coding sequence that is transcribed to produce one or more transcriptional products that produce siRNA in the treated cells.

In another embodiment, the RNAi construct is a hairpin RNA which is processed to an siRNA in the treated cells.

In yet another embodiment, at least a portion of the RNAi construct has a sequence corresponding one or more of TATGGGAACAATTGAAGTAAA (16A-1) (SEQ ID NO.: 1), CAGAAAGTGCCTGACACACTA (16A-2) (SEQ ID NO.:2), CTCGGGATGTTCACAACCGAA (16A+16B-1) (SEQ ID NO.:3), ATGGGTAGGGTAAATCAGTAA (16A+16B-2) (SEQ ID NO.:4) or fragments or variants of any one of SEQ ID NO.: 1, SEQ ID NO.: 2, SEQ ID NO.: 3 or SEQ ID NO.: 4.

In a related embodiment, at least a portion of the RNAi construct is at least about 80% identical to the nucleotide sequence identified by SEQ ID NO.: 5 or fragments or variants thereof. In another related embodiment, at least a portion of the RNAi construct is at least about 90% identical to the nucleotide sequence identified by SEQ ID: SEQ ID NO.: 5 or fragments or variants thereof. In yet another related embodiment, at least a portion of the RNAi construct is at least about 99.9% identical to the nucleotide sequence identified by SEQ ID: SEQ ID NO.: 5 or fragments or variants thereof.

In one embodiment, the RNAi construct has a sequence corresponding one or more of SEQ ID NO.: 5 or fragments or variants thereof. In a related embodiment, the RNAi construct is at least about 80% identical to the nucleotide sequence identified by SEQ ID NO.: 5 or fragments or variants thereof. In another related embodiment, the RNAi construct is at least about 90% identical to the nucleotide sequence identified by SEQ ID NO.: 5 or fragments or variants thereof. In yet another related embodiment, the RNAi construct is at least about 99.9% identical to the nucleotide sequence identified by SEQ ID NO.: 5 or fragments or variants thereof.

Provided herein, according to one aspect, are pharmaceutical compositions comprising a CTNNB1 siRNA construct and a pharmaceutically acceptable carrier.
wherein the construct has a sequence complementary to at least part of CTNNB1 gene.
wherein the construct is an oligonucleotide antisense to CTNNB1 mRNA.

Provided herein, according to one aspect, are kits for treating a CTNNB1 related disease in a subject comprising an RNAi construct and instructions for use.

The invention also provides, according to one aspect, methods of treating a subject, comprising:
(a) determining the pretreatment level of one or more of the following proportions, levels, or cellular localizations, in a cancer cell from the subject:
  (i) the proportion of 16A transcript to 16B transcript,
  (ii) the proportion of cMYC transcript to WAF1 transcript,
  (iii) the level of 16A transcript,
  (iv) the level of 16B transcript,
  (v) the level of cMYC transcript,
  (vi) the level of WAF1 transcript,
  (vii) the proportion of cMYC protein to WAF1 protein,
  (viii) the proportion of CTNNB1 protein to the level of 16A, 16B, cMYC or WAF1 transcripts,
  (ix) the level of cMYC protein,
  (x) the level of WAF1 protein,
  (xi) the level of overall transcription activity, or
  (xii) the cellular localization of the CTNNB1 protein; and
(b) administering a therapeutically effective amount of CTNNB1 related RNAi to the subject, wherein if one or more of the proportions, levels, or cellular localization as measured in one or more of steps (a)(i) through (a)(xii) indicates that treatment with a CTNNB1 related cancer treatment will be efficacious.

In one embodiment, the subject is identified as having cancer or a high-risk lesion (e.g., high-grade dysplasia).

In another embodiment, the initial period of treatment is the time required to achieve a steady-state plasma or cellular concentration of the CTNNB1 RNAi.

Methods may further comprise administration of an additional CTNNB1 therapeutic agent or treatment modality (e.g. esophagectomy, mucosectomy, radiation therapy).

According to one embodiment, the additional CTNNB1 therapeutic agent is an anticancer or chemopreventive agent.

In another embodiment, the additional CTNNB1 therapeutic agent is an anti-inflammatory agent.

Methods of monitoring the progress of a subject being treated with CTNNB1 directed therapy are provided herein, according to one aspect. The methods comprise (a) determining the pre-treatment level of one or more of the proportions, levels, cellular localization, or activities in a cancer cell from the subject, as described above, (b) administering a therapeutically effective amount of a CTNNB1 RNAi to the subject; and (c) determining the level of one or more of the proportions, levels, or cellular localization in the tumor after an initial period of treatment with the CTNNB1 RNAi, wherein a modulation of the proportion, level, cellular localization or activity as measured in one or more of steps (a)(i) through (a)(xii) in the cancer cell following administration of the CTNNB1 RNAi is an indication that the cancer treatment is efficacious.

According to one embodiment, the methods may further comprise administering a second therapeutically effective amount of a CTNNB1 RNAi to the subject; wherein the second therapeutically effective amount of a CTNNB1 RNAi may be the same, or different than the first therapeutically effective amount of a CTNNB1 RNAi; and determining the level of one or more of the proportions, levels, or cellular localization as measured in one or more of steps (a)(i) through (a)(xii) as recited above in the tumor after a second period of treatment with the CTNNB1 RNAi.

Thus, the methods and compositions of the present invention provide and solve the need for methods and compositions useful in therapeutically treating CTNNB1 related diseases and methods of accurately assessing, e.g., diagnostically, prognostically, and therapeutically, CTNNB1 related diseases.

In one embodiment, an increased level of nuclear localization of CTNNB1 correlates with metastasis and/or a decreased prognosis.

In one embodiment, an increase in one or more of the levels of 16B transcript, cMYC transcript or the level of overall transcription activity indicates that the subject may have or is more likely to have progression from adenoma to carcinoma.

Other embodiments of the invention are disclosed infra.

BRIEF DESCRIPTION OF THE DRAWINGS

FIG. 4A depicts a micrograph of a esophageal squamous cell carcinoma in-situ stained with hematoxylin and eosin showing proliferation of immature, dysplastic squamous cells with high nuclear to cytoplasmic ratios, hyperchromasia, irregular nuclear contours and, focally, visible nucleoli, occupying the full thickness of the epithelium.

FIG. 4B shows an adjacent tissue section stained with an immunohistochemical antibody to beta-catenin followed by a chromagen and showing high protein, expression, e.g., intense staining, in this neoplastic lesion.

FIG. 8 is a chart of PCR primers useful in the invention.

FIG. 9 is the nucleotide sequence of SEQ ID NO. 5 representing the nucleotide sequence of the *Homo sapiens* catenin (cadherin-associated protein), beta 1, 88 kDa CTNNB1, mRNA as found in GenBank accession No. NM_001904.

FIG. 10 is SEQ ID. NO. 6, which represents the amino acid translation of the sequence of FIG. 5.

DEFINITIONS

Figure 1:
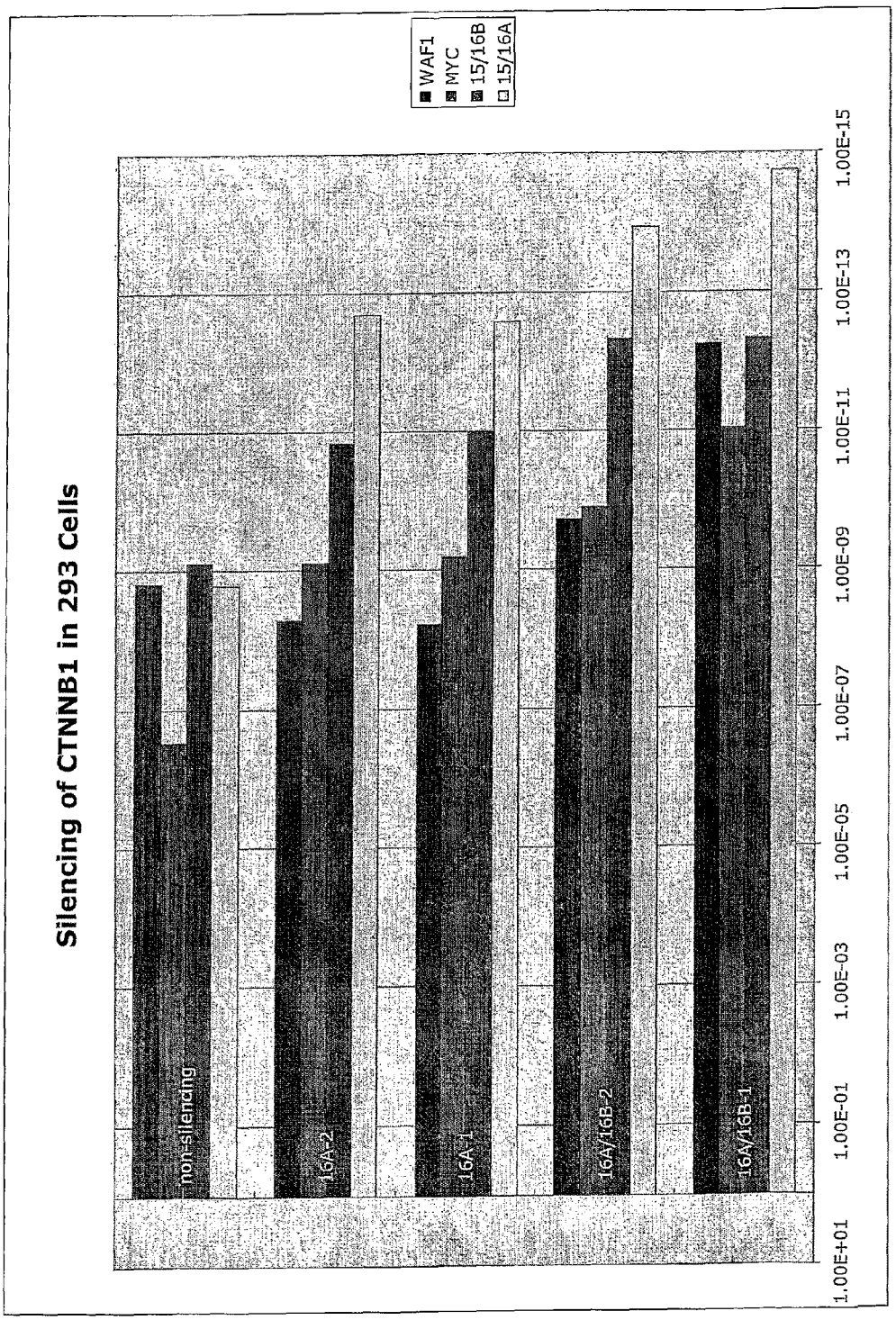
FIG. 1 depicts a striking reduction in both CTNNB1 splice variants with RNAi constructs targeted to 16A-1 or 16A-2. An increase in WAF1 expression and a concomitant decrease in MYC expression resulted in a reduction of the MYC to WAF1 ratio (ratio=<1). The x-axis reflects relative copy numbers for each of the genes assayed (e.g. 15/16A, 15/16B, MYC and WAF1). The non-silencing (top panel) shows high levels of MYC with respect to WAF1 and CTNNB1, with comparable levels of 16A and B splice variants; (16A/16B-1=Entire silencing of CTNNB1; 16A/16B-2=Entire silencing of CTNNB1; 16A-1=Silencing of the 16A transcript variant; 16A-2=Silencing of the 16A transcript variant only; non-Silencing control.
Figure 2:
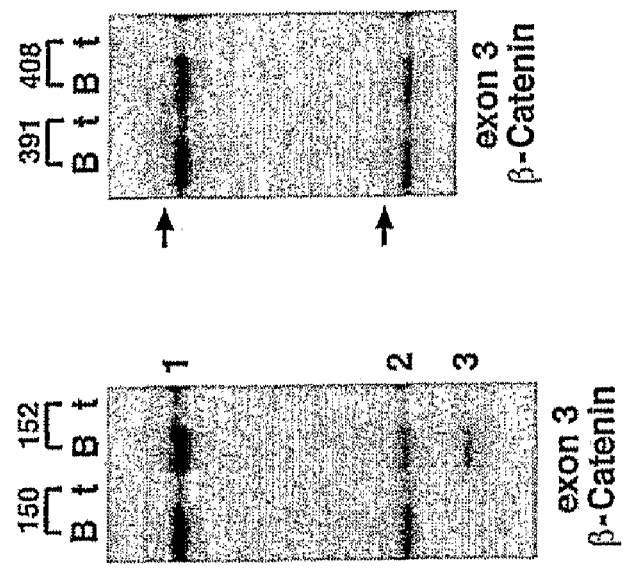
FIG. 2 depicts the results of a mutation analysis performed on matched blood (B) and esophageal squamous cell tumor (t) tissue. Patients were selected from the Shanxi Cancer Hospital in Taiyuan, Shanxi Province, People's Republic of China, after they were diagnosed with esophageal squamous cell carcinoma (ESCC). They were considered candidates for curative surgical resection, were identified and recruited to participate in the study. Ten ml of venous blood and a portion of tumor fixed in ethanol were obtained from 56 patients and analyzed for CTNNB1 exon 3 mutations using SSCP. Genomic and somatic DNA were extracted and purified from venous blood and tumor tissue, respectively, using methods previously described (Hu Cancer Res 2001). Briefly, tumor cells were microdissected under light microscopic visualization, mutations in exon 3 of CTTNB1 were screened by PCR-SSCP using primers (5'-ctaatgctaatactgtttcgt-3' (SEQ ID NO.: 6) and 5'-tactcttaccagctacttgttctt-3' (SEQ ID NO.: 7)) producing a 228 bp PCR product after adjusting the annealing temperature to 53° C. SSCP lanes with blood (B) or tumor (t) DNA from Case No. 150 contain two bands (1 and 2). In contrast, the lane with blood DNA from Case No. 152 has a third band (band 3), consistent with the presence of a germline mutation. Similarly, the lane with tumor DNA from Case No. 391 contains an 'extra' band (arrows) just above each of the two normally present brands, consistent with a somatic mutation. DNA from each of these lanes was subsequently sequenced and both mutations were confirmed.
Figure 3:
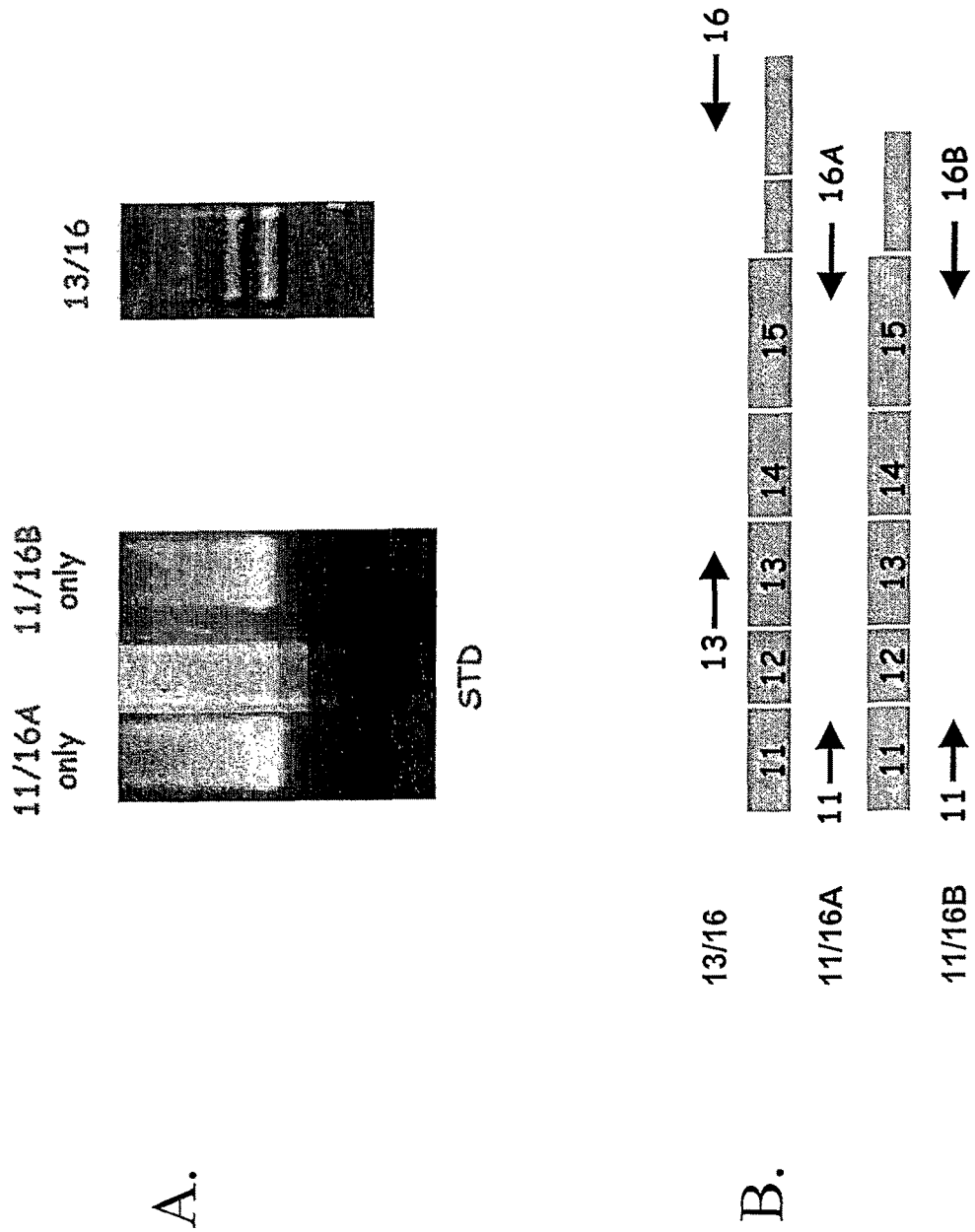
FIG. 3A depicts a gel electrophoretic RT-PCR result with primers extending from exon 11 to 16A, exon 11 to 16B, and exon 13 to exon 16 inclusive.
FIG. 3B is a schematic of 16A and 16B transcripts of the CTNNB1 gene showing the placement of primers for PCR amplification, extending either from exon 13 to 16 (upper right) or exon 11 to 16A or 16B (upper left)
Figure 5:
FIG. 5 depicts a schematic of the β-catenin gene, including numerical labeling for each of its 16 exons.

Unless further defined below all terms as used herein are given their customary meaning. In the case of terms specifically defined below the definitions include their customary meaning but are expanded to include the additional context of the specific definition.

As used herein, and unless otherwise indicated, the term "antisense oligonucleotide" refers to an oligonucleotide having a sequence complementary to a target DNA or RNA sequence.

As used herein, the term "antisense strand" of an siRNA or RNAi agent e.g., an antisense strand of an siRNA duplex or siRNA sequence, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process. The term "sense strand" or "second strand" of an siRNA or RNAi agent e.g., an antisense strand of an siRNA duplex or siRNA sequence, refers to a strand that is complementary to the antisense strand or first strand. Antisense and sense strands can also be referred to as first or second strands, the first or second strand having complementarity to the target sequence and the respective second or first strand having complementarity to said first or second strand.

As used herein, the term "assessing" is intended to include quantitative and qualitative determination in the sense of obtaining an absolute value for the amount or concentration of the analyte present in the sample, and also of obtaining an index, ratio, percentage, visual and/or other value indicative of the level of analyte in the sample. Assessment may be direct or indirect and the chemical species actually detected need not of course be the analyte itself but may for example be a derivative thereof or some further substance.

As used herein, "benign hyperplastic disorders" include, without being limited thereto, benign prostate hyperplasia (BPH), non-tumorigenic polyps in the digestive tract, in the uterus and others.

As used herein, "cellular localization" refers to the localization of a protein or nucleic acid in the cell, (e.g., cytoplasmic versus nuclear).

As used herein, "comparing" in relation to "the proportion, level, or cellular localization, to a standard proportion, level, or cellular localization" refers to making an assessment of the how the proportion, level, or cellular localization of a CTNNB1-related transcript or protein in a sample relates to the proportion, level, or cellular localization of a CTNNB1-related transcript or protein of the standard. For example, assessing whether the proportion, level, or cellular localization of the CTNNB1-related transcript or protein of the sample is the same as, more or less than, or different from the proportion, level, or cellular localization CTNNB1-related transcript or protein of the standard.

When used to describe the sequences of siRNAs, the term "corresponding to," as used herein, means that an siRNA has a sequence that is identical or complementary to the portion of target mRNA that is transcribed from the denoted DNA sequence.

As used herein, and unless otherwise indicated, the term "complementary," when used to describe a sequence in relation to a target sequence, means that the sequence is able to bind to the target sequence in a cellular environment in a manner sufficient to disrupt the function (e.g., replication, splicing, transcription or translation) of the gene comprising the target sequence. The binding may result from interactions such as, but not limited to, nucleotide base parings (e.g., A-T/G-C). In particular embodiments of the invention, a sequence is complementary when it hybridizes to its target sequence under high stringency, e.g., conditions for hybridization and washing under which nucleotide sequences, which are at least 60 percent (preferably greater than about 70, 80, or 90 percent) identical to each other, typically remain hybridized to each other. Such stringent conditions are known to those skilled in the art, and can be found, for example, in Current Protocols in Molecular Biology, John Wiley & Sons, N.Y. (1989), 6.3.1-6.3.6, which is incorporated herein by reference. Another example of stringent hybridization conditions is hybridization of the nucleotide sequences in 6× sodium chloride/sodium citrate (SSC) at about 45 degrees C., followed by 0.2×SSC, 0.1% SDS at 50-65 degrees C. Particularly preferred stringency conditions are hybridization in 6× sodium chloride/sodium citrate (SSC) at about 45 C, followed by one or more washes in 0.2×SSC, 0.1% SDS at 50C. Another example of stringent hybridization conditions are hybridization in 6× sodium chloride/sodium citrate (SSC) at about 45C, followed by one or more washes in 0.2×SSC, 0.1% SDS at 55C. A further example of stringent hybridization conditions are hybridization in 6× sodium chloride/sodium citrate (SSC) at about 45C, followed by one or more washes in 0.2×SSC, 0.1% SDS at 60C. Preferably, stringent hybridization conditions are hybridization in 6× sodium chloride/sodium citrate (SSC) at about 45C, followed by one or more washes in 0.2×SSC, 0.1% SDS at 65C. Another preferred example of stringent hybridization condition is 0.5M sodium phosphate, 7% SDS at 65C, followed by one or more washes at 0.2×SSC, 1% SDS at 65C. Depending on the conditions under which binding sufficient to disrupt the functions of a gene occurs, a sequence complementary to a target sequence within the gene need not be 100 percent identical to the target sequence. For example, a sequence can be complementary to its target sequence when at least about 70, 80, 90, or 95 percent of its nucleotides bind via matched base pairings with nucleotides of the target sequence.

As used herein, "correlating" in reference to a parameter, e.g., a modulated proportion, level, or cellular localization in the cell from the subject, may be an indication that the cancer is likely a CTNNB1 related cancer. "Correlating" or "normalization" as used according to the present invention may be by any method of relating levels of expression or localization of markers to a standard valuable for the: assessment of the diagnosis, prediction of a cancer or cancer progression, assessment of efficacy of clinical treatment, identification of a tumor that may respond to a CTNNB1 treatment, selection of a subject for a particular treatment, monitoring of the progress of treatment with a CTNNB1 directed therapy, and in the context of a screening assay, for the identification of a CTNNB1 related cancer CTNNB1 therapeutic.

The term "CTNNB1-associated signal transduction pathway" refers to any pathway that involves the activation of CTNNB1. Effectors of the pathway include elements of the Wnt pathway and the NF-.kappa.B pathway, but further elements are constantly being discovered and this term covers such newly found elements as well as newly found pathways associated with the CTNNB1 pathway.

A "CTNNB1 related cancer" and "CTNNB1 related disorder" are used interchangeably herein, and include any cancer, pre-cancer, or disorder that involves a change in the expression of the CTNNB1, either at the protein or RNA level. Examples include, esophageal squamous cell carcinoma, gastrointestinal or esophageal adenocarcinoma, gastrointestinal or esophageal dysplasia, gastrointestinal or esophageal metaplasia, Barrett's intestinal tissue, pre-cancerous conditions in histologically normal appearing esophageal squamous mucosa, neoplasias and neoplasia precursor lesions of the cervix, lung, head, and neck—neoplasias and their precursor lesions associated with similar histologically identified lesions, including, squamous cell carcinoma of the cervix, lung, and head and neck.

As used herein, and unless otherwise indicated, the term "CTNNB1 siRNA" denotes a small interfering RNA that has a sequence complementary to a sequence within the CTNNB1 gene. Typically, siRNAs are about 20 to 23 nucleotides in length.

As used herein, the "cell from the subject" may be one or more of a preneoplastic squamous epithelium, a squamous dysplasia, squamous cell carcinoma in-situ, an invasive esophageal squamous cell carcinoma, or any histological or cytological stage in-between.

"Diagnostic" or "diagnosed" means identifying the presence or nature of a pathologic condition. Diagnostic methods differ in their sensitivity and specificity. The "sensitivity" of a diagnostic assay is the percentage of diseased subjects who test positive (percent of "true positives"). Diseased subjects not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, "fresh tumors" refer to tumors removed from a host by surgical or other means.

As used herein, the term "guide strand" refers to a strand of an RNAi agent, e.g., an antisense strand of an siRNA duplex or siRNA sequence, that enters into the RISC complex and directs cleavage of the target mRNA.

A "high-risk lesion" refers to, for example, a high-grade dysplasia.

As used herein, the term "isolated RNA" (e.g., "isolated ssRNA", "isolated siRNA" or "isolated ss-siRNA") refers to RNA molecules which are substantially free of other cellular material, or culture medium when produced by recombinant techniques, or substantially free of chemical precursors or other chemicals when chemically synthesized.

A gene "involved" in a disorder includes a gene, the normal or aberrant expression or function of which effects or causes a disease or disorder or at least one symptom of said disease or disorder.

A gene "involved" in a disease or disorder includes a gene, the normal or aberrant expression or function of which effects or causes the disease or disorder or at least one symptom of said disease or disorder.

As used herein, "marker," and "parameter" refer to one or more of the following: the proportion of 16A transcript to 16B transcript, the proportion of cMYC transcript to WAF1 transcript, the level of 16A transcript, the level of 16B transcript, the level of cMYC transcript, the level of WAF1 transcript, the proportion of cMYC protein to WAF1 protein, the proportion of CTNNB1 protein to one or more of the levels of 16A, 16B, cMYC or WAF1 transcripts, the level of cMYC protein, the level of WAF1 protein, the level of overall transcription activity, or the cellular localization of the CTNNB1 protein.

As used herein, and unless otherwise indicated, the term "inhibiting the synthesis or expression" of a gene means impeding, slowing or preventing one or more steps by which the end-product protein encoded by said gene is synthesized. Typically, the inhibition involves blocking of one or more steps in the gene's replication, transcription, splicing or translation through a mechanism that comprises a recognition of a target site located within the gene sequence based on sequence complementation. In a specific embodiment, inhibition of CTNNB1 reduces the amount of TCTP in the cancer cell by greater than about 20, 50, or 70 percent. The amount of TCTP can be determined by well-known methods including, but are not limited to, densitometer, fluorometer, radiography, luminometer, antibody-based methods and activity measurements.

As used herein, the term "modulated" refers to increases or decreases in the level, activity or proportion of one or more of the parameters, e.g., the increase in the amount of CTNNB1 in the cytoplasm in a cell that is progressing to neoplasia.

As used herein, the term "molecule" when used without other qualification, e.g., nucleic acid molecule, refers to both compounds of biological origin or character (e.g., proteins, DNA, RNA, antibodies, etc.) and compounds which are synthetic organic compounds (e.g., aspirin, ibuprofen, ampicillin, etc.).

As used herein, the term "an oligonucleotide having a nucleotide sequence encoding a gene" means a nucleic acid sequence comprising the coding region of a gene, e.g. the nucleic acid sequence which encodes a gene product. For example, the 16A transcript is an oligonucleotide encoding the CTNNB1 gene. The coding region may be present in a cDNA, genomic DNA or RNA form. When present in a DNA form, the oligonucleotide may be single-stranded (e.g., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

As used herein, and unless otherwise indicated, the term "part," as used to designate a portion of a DNA or RNA, means a portion of at least 15, 20, or 25 nucleotides.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

The term "phosphorylated" means that at least one phosphate group is attached to a chemical (e.g., organic) compound. Phosphate groups can be attached, for example, to proteins or to sugar moieties via the following reaction: free hydroxyl group+phosphate donor.fwdarw.phosphate ester linkage. The term "5'phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). Mono-, di-, and triphosphates are common. Also intended to be included within the scope of the instant invention are phosphate group analogs which function in the same or similar manner as the mono-, di-, or triphosphate groups found in nature (see e.g., exemplified analogs).

The term "polymorphism" refers to the coexistence of more than one form of a gene or portion (e.g., allelic variant) thereof. A portion of a gene of which there are at least two different forms, e.g., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, "a reference cell or population of cells" refers to a cell sample that is clinically normal, clinically somewhere on the continuum between normal and neoplastic, or is neoplastic, depending on the particular methods of use. The reference cell may be, for example, one or more of the following, cells from the subject, cultured cells, cultured cells from the subject, or cells from the subject pre-treatment, for example, a sample from a different portion of the tissue being diagnosed, or from another tissue of the subject. The cells may alternately be from the subject post-treatment. The reference may also be from treated tissue culture cells. The cultures may be primary or established cultures and may be from the subject being diagnosed or from another source. The cultures may be from the same tissue being diagnosed or from another tissue. The cultures may also be normal, anywhere on the continuum from normal to neoplastic, and/or neoplastic.

As used herein, "related clinical intervention" includes, for example, chemoprevention, surgical intervention, radiation therapy or biological therapy.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

By "reduce or inhibit" is meant the ability to cause an overall decrease preferably of 20% or greater, more preferably of 50% or greater, and most preferably of 75% or greater, in the level of protein or nucleic acid, detected by the aforementioned assays (see "expression"), as compared to samples not treated with antisense nucleobase oligomers or dsRNA used for RNA interference.

An siRNA having a "sequence sufficiently complementary to a target mRNA sequence to direct target-specific RNA interference (RNAi)" means that the ss-siRNA has a sequence sufficient to trigger the destruction of the target mRNA by the RNAi machinery or process.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "sample" refers to cells, tissue samples or cell components (such as cellular membranes or cellular components) obtained from the treated subject. By one embodiment the sample are cells known to manifest the disease, for example, where the disease is cancer of type X, the cells are the cells of the tissue of the cancer (breast, colon, skin, liver, lungs, cells, etc.) or metastasis of the above. By another embodiment the sample may be non-diseased cells such as cells obtained from blood for example neutrophils. In other embodiments the sample is a cell from a subject suspected of being cancerous. A cell suspected of being cancerous is characterized as being in a state anywhere along the progression from normal to neoplastic may be determined by methods known in the art, for example, tissue or cellular staining, or any molecular method or pathologic method of diagnosis. Such cell may be determined to be preneoplastic squamous epithelium, a squamous dysplasia, squamous cell carcinoma in-situ, an invasive esophageal squamous cell carcinoma, or any histological or cytological stage in-between.

An RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

By "small interfering RNAs (siRNAs)" (also referred to in the art as "short interfering RNAs") is meant an isolated RNA molecule comprising between about 10-50 nucleotides (or nucleotide analogs) which is capable of directing or mediating RNA interference. The siRNA is preferably greater than 10 nucleotides in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3'hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides. Brummelkamp et al., Science 296:550-553 (2002); Lee et al, (2002). supra; Miyagishi and Taira, Nature Biotechnol. 20:497-500 (2002); Paddison et al. (2002), supra; Paul (2002), supra; Sui (2002) supra; Yu et al. (2002), supra.

siRNA also includes "single-stranded small interfering RNA molecules." "Single-stranded small interfering RNA molecules" ("ss-siRNA molecules" or "ss-siRNA"). ss-siRNA is an active single stranded siRNA molecule that silences the corresponding gene target in a sequence specific manner. Preferably, the ss-siRNA molecule has a length from about 10-50 or more nucleotides. More preferably, the ss-siRNA molecule has a length from about 19-23 nucleotides. In addition to compositions comprising ss-siRNA molecules other embodiments of the invention include methods of making said ss-siRNA molecules and methods (e.g., research and/or therapeutic methods) for using said ss-siRNA molecules.

The term "solid tumors" refers to carcinomas, sarcomas, adenomas, and cancers of neuronal origin and, in fact, to any type of cancer which does not originate from the hematopoietic cells and in particular concerns: carcinoma, sarcoma, adenoma, hepatocellular carcinoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, synovioma, Ewing's tumor, leiomyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

As used herein, the term "specifically hybridizes" or "specifically detects" refers to the ability of a nucleic acid molecule to hybridize to at least approximately 6 consecutive nucleotides of a sample nucleic acid.

The terms "subject" or "patient" are used interchangeably herein, and is meant a mammalian subject to be treated, with human subjects being preferred. In some cases, the methods of the invention find use in experimental animals, in veterinary application, and in the development of animal models for disease, including, but not limited to, rodents including mice, rats, and hamsters; and primates.

As used herein, "substantial sequence identity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial sequence identity exists when the segments will hybridize under selective hybridization conditions, to a strand, or its complement, typically using a fragment derived from the known nucleotide sequence of the CTNNB1-related gene. Typically selective hybridization will occur when there is at least about 55% sequence identity over a stretch of at least about 14 nucleotides, preferably at least about 65%, more preferably at least about 75%, and most preferably at least about 90%. See Kanehisa (1984) Nuc. Acids Res. 12:203-213. The length of sequence identity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations. In determining sequence identity or percent homology the below discussed protocols and programs for sequence similarity are suitably employed including the BLAST algorithm.

"Substantially purified" refers to nucleic acid molecules or proteins that are removed from their natural environment and are isolated or separated, and are at least about 60% free, preferably about 75% free, and most preferably about 90% free, from other components with which they are naturally associated.

As used herein, and unless otherwise indicated, the term "suppression" or "suppressing", when used in relation to the growth of a cell, means retardation or prevention of the growth of the cell. Such suppression may be, but is not necessarily, accomplished through mechanisms such as, but not limited to, tumor reversion and cell apoptosis. In specific embodiments of this invention, growth of a cell is suppressed when the growth is slowed by greater than about 20, 30, 50, 75, 100 or 200 percent as determined by, e.g., mass tumor volume.

A "surrogate cell" as used herein may be a preneoplastic cell or it may be a reference cell.

A "target gene" is a gene whose expression is to be selectively inhibited or "silenced." This silencing is achieved by cleaving the mRNA of the target gene by an siRNA that is created from an engineered RNA precursor by a cell's RNAi system. One portion or segment of a duplex stem of the RNA precursor is an anti-sense strand that is complementary, e.g., fully complementary, to a section of about 18 to about 40 or more nucleotides of the mRNA of the target gene.

"A tumor that responds" refers to a change in the tumor as a result of a treatment, for example, a reduction or stability in growth or invasive potential of the tumor, e.g., a favorable response. A tumor is also considered to respond if it increases or if it becomes more unstable, or exhibits metastasis, e.g. an unfavorable response.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

DETAILED DESCRIPTION

β-catenin is a key component of certain cellular signaling pathways leading to activation of gene expression and a variety of developmental and disease processes, such as cellular differentiation, cancer and Alzheimer's disease. In particular, CTNNB1 functions in Wnt-mediated signaling, and associates with LEF-1/TCF DNA binding proteins to form a transcription factor (see Willert and Nusse, Genetics and Development 8:95-102, 1998). β-catenin-mediated signaling is involved in a variety of developmental processes, including cellular differentiation and growth. For example, see (Gat et al., Cell 95:605-614, 1998; Ono et al., Cell 95:575-578, 1998). Diagnostic and screening assays based on β-catenin have clinical significance because of disease states associated with β-catenin, e.g., certain cancers and Alzheimer's disease.

β-catenin is located in a chromosomal region (3p) that is associated with both early and late genetic events of esophageal squamous cell carcinogenesis, and its protein appears to be overexpressed with neoplastic progression (Iwamoto, D D W 2003; Roth, Cancer Detection and Prevention 2002; and Roth, Cancer Research 2001). Other studies of esophageal cancer show similar overexpression of CTNNB1 competing for binding partners such as APC (Kimura Int. J. Cancer 1999, Osterheld Am J Clin Pathol 2002) and, subsequently, stabilization of excess β-catenin which is then available to be translocated to the nucleus (Bienz and Clevers Nature 2003). Despite finding generalized CTNNB1 overexpression and genetic changes on 3p, it is still not clear whether alteration in the expression of CTNNB1, downstream targets and/or nuclear or cytoplasmic localization of CTNNB1 are associated with the development of ESCC. These potential associations are further complicated by CTNNB1 alternative splice forms as initially described by Nollet et al.

Genomic cloning shows the CTNNB1 locus to consist of 16 exons stretching over a region of 23 kb and carrying a splice variant (16B) for a truncated portion of the non-coding region of exon 16 (Nollet Genomics 1996). In a small set of human colon cancer cell lines, both the wild type and variant have been identified at similar levels by RT-PCR. However, this variant has not been studied in the setting of ESCC neoplasia, where it may be biologically significant given that the 3' untranslated regions (UTRs) may possess translational control of regulatory elements, which may govern the spatial and temporal expression of mRNA (Mendez Nature 2001, Kuersten Nature Genetics 2003, Hu Molecular Pharmacology 2002).

As an adherins junction or zonula adherens protein, CTNNB1 is associated with cell signaling through the APC or Wnt pathways, with complex binding of E-cadherin, APC, TCF, AXIN, GSK-3B and A-catenin. Some of the functions of CTNNB1 include mediating adhesion between cells and subsequently regulating normal cell growth and behavior, including embryogenesis, wound healing, and tumor metastasis. The later is, in part, related to the participation of CTNNB1 in transcription via interaction with the T-cell family (TCF) of transcription factors. Stabilized CTNNB1 interacts with TCF and activates transcription of downstream target genes such as c-MYC and WAF1 (He Science 1998, Bieche Cancer Res 1999). Degradation of β-catenin requires a multi-protein complex that includes APC and the serine/threonine kinase GSK3 β (Behrens Ann N Y Acad Sci 2000). In tumors, this degradation can be blocked by mutations typically involving exon 3 of the CTTNB1 gene (Behrens Ann N Y Acad Sci 2000).

We describe herein, inter alia, novel methods or assays for accurately and quickly diagnosing and monitoring the progression of β-catenin (CTNNB1) related disorders, such as cancer and its related preneoplastic lesions, and Alzheimer's disease. In particular, the expression and/or localization of certain transcripts and/or proteins are diagnostic of the state of a cellular sample. In addition to methods useful as assessment tools prior to and in parallel with treatment the invention also provides methods of treatment (and prophylaxis) by administration to a subject of an effective amount of a CTNNB1 therapeutic of the invention, e.g., a compound identified by the screening methods of the present invention.

In some embodiments, the present invention involves expression analysis of the CTNNB1 transcript variants and the expression of downstream targets such as MYC and WAF1 across the neoplastic progression of ESCC and related neoplasms. In these embodiments, as well as other embodiments, samples comprising cells, suspected of being cancerous, may be taken from a subject. The cell from the subject suspected of being cancerous may exist anywhere along the progression from normal to neoplastic. For example, such a cell is not normal, and may exhibit signs of dysplasia, or any other pathology between normal and neoplasia.

In some embodiments a cancer cell or surrogate cell may be, for example, one or more of a preneoplastic squamous epithelium, a squamous dysplasia, squamous cell carcinoma in-situ, an invasive esophageal squamous cell carcinoma, or any histological or cytological stage in-between.

Once obtained, the results of any assay herein may be reported to the subject or a health care professional, e.g., reporting the proportion, level, cellular localization, activity, or correlations. The health care professional may then use this information to make a diagnosis or to assess the likelihood that a certain treatment regimen may be efficacious and then initiate treatment.

Following diagnosis or assessment of likelihood of an efficacious result, the treatment may include surgery, focal therapy (mucosectomy, argon plasma coagulator, cryotherapy), selenium fortification, celecoxib, chemoradiation therapy, chemotherapy, including but not limited to, fluorouracil (5-FU), cisplatin, vinblastine, paclitaxel, depsipeptides, flavopiridol, melphalan, and decitabine. The appropriate treatment for a subject may be determined by one of skill in the art.

The identification of those patients who are in need of prophylactic treatment for cancer is well within the ability and knowledge of one skilled in the art. Certain of the methods for identification of patients which are at risk of developing cancer which can be treated by the subject method are appreciated in the medical arts, such as family history, travel history and expected travel plans, the presence of risk factors associated with the development of that disease state in the subject patient. A clinician skilled in the art can readily identify such candidate patients, by the use of, for example, clinical tests, physical examination and medical/family/travel history.

The present invention is further directed to the compounds identified by the screening assays described herein and to processes for producing such agents by use of these assays. In a preferred aspect, the compound is a CTNNB1 therapeutic which is substantially purified. The compounds can include, but are not limited to, nucleic acids, antisense nucleic acids, ribozyme, triple helix, antibody, and polypeptide molecules and small inorganic or organic molecules. Accordingly, in one embodiment, the present invention includes a compound obtained by a method comprising the steps of any one of the screening assays described herein. For example, the compound is obtained by a method comprising contacting a cell, or a fraction thereof, (e.g., lysate) with one or more candidate molecules; and detecting localization of CTNNB1 molecules in the cell, or determining one of the other herein described parameters.

Once a test compound has been identified as having an appropriate activity according to the screening methods of the present invention, the test compound can be subject to further testing, for example, in animal models to confirm its activity as a CTNNB1 related cancer CTNNB1 therapeutic. The test compound can also be tested against known compounds that modulate one of the parameters, in cell based or animal assays, to confirm its desired activity. The identified compound can also be tested to determine its toxicity, or side effects that could be associated with administration of such compound. Alternatively, a compound identified as described herein can be used in an animal model to determine the mechanism of action of such a compound.

In a particular embodiment, the present invention provides a method for treating a disease or disorder characterized by aberrant subcellular localization of CTNNB1. The method comprises administering to a subject having such disease or disorder a composition comprising a molecule that reduces CTNNB1 nuclear localization and a pharmaceutically acceptable carrier. The subject is preferably an animal including, but not limited to animals such as cows, pigs, horses, chickens, cats, dogs, etc., and is preferably a mammal, and most preferably human. In a specific embodiment, a non-human mammal is the subject.

In still further embodiments the methods of the claimed invention may be used to monitor the course of treatment or status of a subject. Monitoring of a subject is undertaken "after an initial period of treatment" or after an appropriate period of time after the administration of a CTNNB1 related cancer therapy, e.g., 2 hours, 4 hours, 8 hours, 12 hours, or 72 hours, weeks, or months. During this post-treatment monitoring one or more of the proportions, levels, and/or cellular localization may be determined again. The modulation of one or more of the proportions, levels, and/or cellular localization of CTNNB1-related transcripts or proteins may indicate efficacy of an anti-cancer treatment. One or more of the proportions, levels, and/or cellular localization of CTNNB1-related transcripts or proteins may be determined periodically throughout treatment. For example, one or more of the proportions, levels, and/or cellular localization of the CTNNB1-related transcript or protein may be checked every few hours, days or weeks to assess the further efficacy of the treatment. The method described may be used to screen or select patients that may benefit from treatment with a CTNNB1 related therapy.

The initial period of treatment may be the time required to achieve a steady-state plasma or cellular concentration of the CTNNB1 related cancer treatment. The initial period may also be the time to achieve a modulation in one or more proportions, levels, or cellular localizations of CTNNB1-related transcripts or proteins.

Treatment of a subject may entail administering more than one dose of a CTNNB1 therapeutically effective amount of a CTNNB1 cancer treatment. Between doses, it may be desirable to determine the level of one or more of the proportions, levels, or cellular localization of CTNNB1-related transcripts or proteins in the tumor after a second period of treatment with the CTNNB1 related cancer treatment. This is one example of how a treatment course may be monitored to determine if it continues to be efficacious for the subject. When monitoring the treatment, it may be desirable to comparing one or more of the pre-treatment or post-treatment proportions, levels, or cellular localization of CTNNB1-related transcripts or proteins to a standard proportion, level, or the cellular localization of the CTNNB1-related transcripts or proteins.

Treatment may also entail the administration of an additional CTNNB1 therapeutic agent or treatment modality (e.g., esophagectomy, mucosectomy, radiation therapy, chemo or immunotherapy).

In a further embodiment the invention includes kits which contain components specifically useful in the methods described herein. One example of the types of kits contemplated in this application is a kit for determining a subject's response to a CTNNB1-directed therapy. Such a kit for determining a response to a CTNNB1-directed therapy in a subject may comprise at least two reagents that determine one or more of the parameters.

Kits, according to the invention, may include reagents, including primers, polymerases, antibodies, buffers, and/or labels. The kit may also include microscope slides, reaction vessels, instruction for use of the reagents and material and how to interpret the data generated from the assays. For example, PCR primers for the amplification of the 16A, 16B, cMYC or WAF1 transcripts may be included. Antibodies to detect the CTNNB1 protein may also be included in the kit.

Compositions Useful in Practicing CTNNB1-Related Methods

Proteins and Polynucleotides

The CTNNB1-related methods as described in this application may utilize or measure the levels of CTNNB1-related proteins. These CTNNB1-related proteins may be naturally occurring, synthetic or recombinant in nature.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

The terms "protein" and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, mimetopes and peptidomimetics. Methods for preparing mimetopes and peptidomimetics are known in the art.

The terms "mimetope" and "peptidomimetic" are used interchangeably herein. A "mimetope" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260:1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide. Examples of amino acid mimetics include D-amino acids. Peptides substituted with one or more D-amino acids may be made using well-known peptide synthesis procedures. Additional substitutions include amino acid analogs having variant side chains with functional groups, for example, b-cyanoalanine, canavanine, djenkolic acid, norleucine, 3-phosphoserine, homoserine, etc.

Preferred amino acids include the naturally occurring amino acids, as well as synthetic derivatives, and amino acids derived from proteins, e.g., proteins such as casein, e.g., casamino acids, or enzymatic or chemical digests of, e.g., yeast, an animal product, e.g., a meat digest, or a plant product, e.g., soy protein, cottonseed protein, or a corn steep liquor (see, e.g., Traders' Guide to Fermentation Media, Traders Protein, Memphis, Tenn. (1988), Biotechnology: A Textbook of Industrial Microbiology, Sinauer Associates, Sunderland, Mass. (1989), and Product Data Sheet for Corn Steep Liquor, Grain Processing Corp., IO).

The term "naturally occurring amino acid" includes any of the 20 amino acid residues which commonly comprise most polypeptides in living systems, rarer amino acids found in fibrous proteins (e.g., 4-hydrorxyproline, 5-hydroxylysine, —N-methyllysine, 3-methylhistidine, desmosine, isodesmosine), and naturally occurring amino acids not found in proteins (e.g., -alanine, -aminobutryic acid, homocysteine, homoserine, citrulline, ornithine, canavanine, djenkolic acid, and -cyanoalanine).

The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See http://www.ncbi.nlm.nih.gov.

Sequence similarity searches can be also performed manually or by using several available computer programs mown to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. The GCG Package provides a local version of Blast that can be used either with public domain databases or with any locally available searchable database. GCG Package v9.0 is a commercially available software package that contains over 100 inter-related software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for sequence identity searching, gene finding, multiple sequence alignment, secondary structure prediction, and motif identification. GeneThesaurus 1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Antibodies

Antibodies which bind to specific CTNNB1-related proteins are also useful in preparing compositions or methods as described in this application. Various procedures known in the art may be used for the production of antibodies to CTNNB1, CTNNB1 family members or any subunit thereof, or CTNNB1, or a fragment, derivative, homolog or analog of the protein. Antibodies of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

For production of the antibody, various host animals can be immunized by injection with, e.g., a native CTNNB1 protein or a synthetic version, or a derivative of the foregoing. Such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *Corynebacterium parvum*. Although the following refers specifically to CTNNB1, any of the methods described herein apply equally to CTNNB1, CTNNB1 family members or subunits thereof, or CTNNB1.

For preparation of monoclonal antibodies directed towards CTNNB1 or a derivative, fragment, homolog or analog thereof, any technique that provides for the production of antibody molecules by continuous cell lines in culture may be used. Such techniques include, but are not restricted to, the hybridoma technique originally developed by Kohler and Milstein (1975, Nature 256:495-497), the trioma technique (Gustafsson et al., 1991, Hum. Antibodies Hybridomas 2:26-32), the human B-cell hybridoma technique (Kozbor et al., 1983, Immunology Today 4:72), and the EBV hybridoma technique to produce human monoclonal antibodies (Cole et al., 1985, In: Monoclonal Antibodies and Cancer Therapy, Alan R. Liss, Inc., pp. 77-96). In an additional embodiment of the invention, monoclonal antibodies can be produced in germ-free animals utilizing recent technology described in International Patent Application PCT/US90/02545.

According to the present invention, human antibodies may be used and can be obtained by using human hybridomas (Cote et al., 1983, Proc. Natl. Acad. Sci. USA 80:2026-2030) or by transforming human B cells with EBV virus in vitro (Cole et al., 1985, In: Monoclonal Antibodies and Cancer Therapy, Alan R. Liss, Inc., pp. 77-96). In fact, according to the invention, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454) by splicing the genes from a mouse antibody molecule specific for CTNNB1 together with genes from a human antibody molecule of appropriate biological activity can be used; such antibodies are within the scope of this invention.

According to the present invention, techniques described for the production of single chain antibodies (U.S. Pat. No. 4,946,778) can be adapted to produce CTNNB1-specific antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for CTNNB1 proteins, derivatives, or analogs thereof. Non-human antibodies can be "humanized" by known methods (e.g., U.S. Pat. No. 5,225,539).

Antibody fragments that contain the idiotypes of CTNNB1 can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

In the production of antibodies, screening for the desired antibody can be accomplished by techniques known in the art, e.g., ELISA (enzyme-linked immunosorbent assay). To select antibodies specific to a particular domain of CTNNB1, or a derivative, homolog, or analog thereof, one may assay generated hybridomas for a product that binds to the fragment of the CTNNB1 protein, or a derivative, homolog, or analog thereof, that contains such a domain.

An "epitope", as used herein, is a portion of a polypeptide that is recognized (e.g., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full-length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

RNAi Compositions for Targeting CTNNB1 mRNA

This invention is generally related to treatment and management of cancer by inhibiting the expression of CTNNB1, which is involved in tumorigenesis. Therefore, one embodiment of this invention is directed to a methods of suppressing the growth of a cancer cell, comprising contacting the cell with a compound that inhibits the synthesis or expression of CTNNB1 gene in an amount sufficient to cause such inhibition. Without being limited by theory, the inhibition is achieved through selectively targeting CTNNB1 DNA or mRNA, e.g., by impeding any steps in the replication, transcription, splicing or translation of the CTNNB1 gene. The sequence of CTNNB1 is disclosed in GenBank Accession No. NM_001904 (SEQ. ID NO.5), the entirety of which is incorporated herein by reference.

RNAi is a remarkably efficient process whereby double-stranded RNA (dsRNA) induces the sequence-specific degradation of homologous mRNA in animals and plant cells (Hutvagner and Zamore (2002), Curr. Opin. Genet. Dev., 12, 225-232; Sharp (2001), Genes Dev., 15, 485-490). In mammalian cells, RNAi can be triggered by 21-nucleotide (nt) duplexes of small interfering RNA (siRNA) (Chiu et al. (2002), Mol. Cell., 10, 549-561; Elbashir et al. (2001), Nature, 411, 494-498), or by micro-RNAs (miRNA), functional small-hairpin RNA (shRNA), or other dsRNAs which are expressed in-vivo using DNA templates with RNA polymerase III promoters (Zeng et al. (2002), Mol. Cell, 9, 1327-1333; Paddison et al. (2002), Genes Dev., 16, 948-958; Lee et al. (2002), Nature Biotechnol., 20, 500-505; Paul et al. (2002), Nature Biotechnol., 20, 505-508; Tuschl, T. (2002), Nature Biotechnol., 20, 440-448; Yu et al. (2002), Proc. Natl. Acad. Sci. USA, 99(9), 6047-6052; McManus et al. (2002), RNA, 8, 842-850; Sui et al. (2002), Proc. Natl. Acad. Sci. USA, 99(6), 5515-5520.)

The present invention features "small interfering RNA molecules" ("siRNA molecules" or "siRNA"), methods of making said siRNA molecules and methods (e.g., research and/or therapeutic methods) for using said siRNA molecules. An siRNA molecule of the invention is a duplex consisting of a sense strand and complementary antisense strand, the antisense strand having sufficient complementary to a target mRNA to mediate RNAi. Preferably, the strands are aligned such that there are at least 1, 2, or 3 bases at the end of the strands which do not align (e.g., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, e.g., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to, e.g., at least 80% (or more, e.g., 85%, 90%, 95%, or 100%) complementary to, e.g., having 3, 2, 1, or 0 mismatched nucleotide(s), a target region, such as a target region that differs by at least one base pair between the wild type and mutant allele, e.g., a target region comprising the gain-of-function mutation, and the other strand is identical or substantially identical to the first strand. small interfering RNA molecules In one embodiment, the expression of CTNNB1 is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA. See, e.g., Hammond et al., Nature Rev Gen 2: 110-119 (2001); Sharp, Genes Dev 15: 485-490 (2001), both of which are incorporated herein by reference in their entireties.

Methods and procedures for successful use of RNAi technology are well-known in the art, and have been described in, for example, Waterhouse et al., Proc. Natl. Acad. Sci. USA 95(23): 13959-13964 (1998). The siRNAs of this invention encompass any siRNAs that can modulate the selective degradation of CTNNB1 mRNA.

The siRNA of the invention include "double-stranded small interfering RNA molecules" ("ds-siRNA" and "single-stranded small interfering RNA molecules" ("ss-siRNA"), methods of making the siRNA molecules and methods (e.g., research and/or therapeutic methods) for using the siRNA molecules.

Similarly to the ds-siRNA molecules, the ss-siRNA molecule has a length from about 10-50 or more nucleotides. More preferably, the ss-siRNA molecule has a length from about 15-45 nucleotides. Even more preferably, the ss-siRNA molecule has a length from about 19-40 nucleotides. The ss-siRNA molecules of the invention further have a sequence that is "sufficiently complementary" to a target mRNA sequence to direct target-specific RNA interference (RNAi), as defined herein, e.g., the ss-siRNA has a sequence sufficient to trigger the destruction of the target mRNA by the RNAi machinery or process. The ss-siRNA molecule can be designed such that every residue is complementary to a residue in the target molecule. Alternatively, substitutions can be made within the molecule to increase stability and/or enhance processing activity of said molecule. Substitutions can be made within the strand or can be made to residues at the ends of the strand. The 5'-terminus is, most preferably, phosphorylated (e.g., comprises a phosphate, diphosphate, or triphosphate group). The 3' end of an siRNA may be a hydroxyl group in order to facilitate RNAi, as there is no requirement for a 3' hydroxyl group when the active agent is a ss-siRNA molecule. Featured are ss-siRNA molecules wherein the 3' end (e.g., C3 of the 3' sugar) lacks a hydroxyl group (e.g., ss-siRNA molecules lacking a 3' hydroxyl or C3 hydroxyl on the 3' sugar (e.g., ribose or deoxyribose).

The siRNAs of this invention include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the action of one or more endogenous enzymes.

The siRNAs of this invention can be enzymatically produced or totally or partially synthesized. Moreover, the siRNAs of this invention can be synthesized in vivo or in vitro. For siRNAs that are biologically synthesized, an endogenous or a cloned exogenous RNA polymerase may be used for transcription in vivo, and a cloned RNA polymerase can be used in vitro. siRNAs that are chemically or enzymatically synthesized are preferably purified prior to the introduction into the cell.

Although 100 percent sequence identity between the siRNA and the target region is preferred, it is not required to practice this invention. siRNA molecules that contain some degree of modification in the sequence can also be adequately used for the purpose of this invention. Such modifications include, but are not limited to, mutations, deletions or insertions, whether spontaneously occurring or intentionally introduced. Specific examples of siRNAs that can be used to inhibit the expression of CTNNB1 are described in detail in Example 5.

The target RNA cleavage reaction guided by siRNAs is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of a siRNA contribute equally to target recognition. Mismatches in the center of the siRNA are most critical and essentially abolish target RNA cleavage. In contrast, the 3' nucleotides of the siRNA do not contribute significantly to specificity of the target recognition. In particular, residues 3' of the siRNA sequence which is complementary to the target RNA (e.g., the guide sequence) are not critical for target RNA cleavage.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (e.g., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (e.g., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (e.g., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (e.g., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the ss-siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50 degrees C. or 70 degrees C. hybridization for 12-16 hours; followed by washing). Additional preferred hybridization conditions include hybridization at 70 degrees C. in 1×SSC or 50 degrees C. in 1×SSC, 50% formamide followed by washing at 70 degrees C. in 0.3×SSC or hybridization at 70 degrees C. in 4×SSC or 50 degrees C. in 4×SSC, 50% formamide followed by washing at 67 degrees C. in 1×SSC. The hybridization temperature for hybrids anticipated to be less than 50 base pairs in length should be 5-10 degrees C. less than the melting temperature (Tm) of the hybrid, where Tm is determined according to the following equations. For hybrids less than 18 base pairs in length, Tm(degrees C.)=2(# of A+T bases)+4(# of G+C bases). For hybrids between 18 and 49 base pairs in length, Tm(degrees C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

In a preferred aspect, the RNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

In an embodiment of the present invention the RNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (e.g., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, e.g., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., $N$6-methyl adenosine are suitable. It should be noted that the above modifications may be combined.

The nucleic acid compositions of the invention include both siRNA and siRNA derivatives as described herein. For example, cross-linking can be employed to alter the pharmacokinetics of the composition, for example, to increase half-life in the body. Thus, the invention includes siRNA derivatives that include siRNA having two complementary strands of nucleic acid, such that the two strands are crosslinked. The invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other Compositions for Targeting CTNNB1 DNA or mRNA

Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site, impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins.

Antisense oligonucleotides of this invention include oligonucleotides having modified sugar-phosphodiester backbones or other sugar linkages, which can provide stability against endonuclease attacks. This invention also encompasses antisense oligonucleotides that are covalently attached to an organic or other moiety that increase their affinity for a target nucleic acid sequence. Agents such as, but not limited to, intercalating agents, alkylating agents, and metal complexes can be also attached to the antisense oligonucleotides of this invention to modify their binding specificities.

A preferred antisense oligonucleotide is a cDNA that, when introduced into a cancer cell, transcribes into an RNA molecule having a sequence complementary to at least part of the CTNNB1 mRNA, e.g., oligonucleotides complementary to the 16A/16B splice variants.

Ribozymes are enzymatic RNA molecules capable of catalyzing the specific cleavage of RNA. The characteristics of ribozymes are well-known in the art. See, e.g., Rossi, Current Biology 4: 469-471 (1994), the entirety of which is incorporated herein by reference. Without being limited by theory, the mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage, which was disclosed in U.S. Pat. No. 5,093,246, the entirety of which is incorporated herein by reference. If the sequence of a target mRNA is known, a restriction enzyme-like ribozyme can be prepared using standard techniques.

The expression of the CTNNB1 gene can also be inhibited by using triple helix formation. Nucleic acid molecules to be used in triple helix formation for the inhibition of transcription should be single stranded and composed of deoxynucleotides. The base composition of these oligonucleotides must be designed to promote triple helix formation via Hoogsteen base paring rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarily to a purine-rich region of a single strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The expression of CTNNB1 can be also inhibited by what is referred to as "co-repression." Co-repression refers to the phenomenon in which, when a gene having an identical or similar to the target sequence is introduced to a cell, expression of both introduced and endogenous genes becomes repressed. This phenomenon, although first observed in plant system, has been observed in certain animal systems as well. The sequence of the gene to be introduced does not have to be identical to the target sequence, but sufficient homology allows the co-repression to occur. The determination of the extent of homology depends on individual cases, and is within the ordinary skill in the art.

It would be readily apparent to one of ordinary skill in the art that other methods of gene expression inhibition that selectively target a DNA or mRNA can also be used in connection with this invention without departing from the gist of this invention.

Methods Involving the RNA Targeting Compositions

Delivery

Delivery of the compositions of this invention (e.g., antisense oligonucleotides, siRNAs, or other compositions described herein) into a patient can either be direct, e.g., the patient is directly exposed to the compositions of this invention or compound-carrying vector, or indirect, e.g., cells are first transformed with the compositions of this invention in vitro, then transplanted into the patient for cell replacement therapy. These two approaches are known as in vivo and ex vivo therapy, respectively.

In the case of in vivo therapy, the compositions of this invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector (U.S. Pat. No. 4,980,286, for example), by direct injection of naked DNA, by use of microparticle bombardment (for example, a gene gun; Biolistic®, DuPont), by coating with lipids or cell-surface receptors or transfecting agents, encapsulation in liposomes, microparticles, or microcapsules, by administering them in linkage to a peptide which is known to enter the cell or nucleus, or by administering them in linkage to a ligand subject to receptor-mediated endocytosis (Wu and Wu, J Biol. Chem. 262:4429-4432 (1987)), which can be used to target cell types specifically expressing the receptors. Further, the compositions of this invention can be targeted in vivo for cell specific uptake and expression, by targeting a specific receptor, as disclosed in, for example, WO 92/06180, WO 92/22635, WO92/20316, WO93/14188, and WO 93/20221. All of these references are incorporated herein by reference.

Ex vivo therapy involves transferring the compositions of this invention to cells in tissue culture by methods such as electroporation, lipofection, calcium phosphate mediated transfection, and viral infection. Usually, the method of transfer includes the transfer of a selectable marker to the cells. The cells are then placed under selection to isolate those cells that have taken up and are expressing the transferred compositions. Those cells are then delivered to a patient.

The compositions of this invention are introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, and spheroplast fusion. Numerous techniques are known in the art for the introduction of foreign compositions into cells. Examples of such techniques are disclosed in: Loeffler et al., Meth. Enzymol. 217:599-618 (1993); and Cohen et al., Meth. Enzymol. 217:618-644 (1993); and Cline, Pharmac. Ther. 29:69-92 (1985), all of which are incorporated herein by reference. These techniques should provide for the stable transfer of the compositions of this invention to the cell, so that they are expressible by the cell and preferably heritable and expressible by its cell progeny.

The resulting recombinant cells can be delivered to a patient by various methods known in the art. Examples of the delivery methods include, but are not limited to, subcutaneous injection, skin graft, and intravenous injection.

The nucleic acid compositions of the invention include both siRNA and siRNA derivatives as described herein. For example, cross-linking can be employed to alter the pharmacokinetics of the composition, for example, to increase half-life in the body. Thus, the invention includes siRNA derivatives that include siRNA having two complementary strands of nucleic acid, such that the two strands are crosslinked. The invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Synthetic siRNAs can be delivered into cells by methods known in the art, including cationic liposome transfection and electroporation. However, these exogenous siRNA generally show short term persistence of the silencing effect (4 to about 5 days in cultured cells), which may be beneficial in only certain embodiments. To obtain longer term suppression of the target genes (e.g., mutant genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., J. Cell. Physiol. 177:206213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expressing T7 RNA polymerase (Jacque (2002), supra). A single construct may contain multiple sequences coding for siRNAs, such as multiple regions of the gene encoding mutant SOD1, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in-vivo reduction of target gene expression. Id. In an animal model, whole-embryo electroporation can efficiently deliver synthetic siRNA into post-implantation mouse embryos (Calegari et al., Proc. Natl. Acad. Sci. U.S. Pat. No. 99(22):14236-40 (2002)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)). Nanoparticles and liposomes can also be used to deliver siRNA into animals.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (e.g., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include *arabidopsis*; field crops; vegetable crops; fruit and nut crops; and ornamentals. Examples of vertebrate animals include fish, mammal, cattle, goat, pig, sheep, rodent, hamster, mouse, rat, primate, and human; invertebrate animals include nematodes, other worms, *drosophila*, and other insects.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of ss-siRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

Design and Production of the RNAi Compositions

One or more of the following guidelines may be used in designing the sequence of siRNA and other nucleic acids designed to bind to a target mRNA, e.g., shRNA, stRNA, antisense oligonucleotides, ribozymes, and the like, that are advantageously used in accordance with the present invention:

Beginning with the AUG start codon of a gene, look for AA dinucleotide sequences; each AA and the 3' adjacent 16 or more nucleotides are potential siRNA targets. The siRNA should be specific for a target region that differs by at least one base pair between the wild type and mutant allele or between splice variants. In dsRNAi, the first strand should be complementary to this sequence, and the other strand identical or substantially identical to the first strand. In one embodiment, the nucleic acid molecules are selected from a region of the 16A or 16B splice variants of CTNNB1. Further, siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules may have a 3' overhang of 2 nucleotides, such as TT. The overhanging nucleotides may be either RNA or DNA. As noted above, it is desirable to choose a target region wherein the mismatch is a purine:purine mismatch.

Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website (http://www.ncbi.nih.gov). Select one or more sequences that meet your criteria for evaluation.

Another method includes, selecting in the sequence of the target mRNA, a region located from about 50 to about 100 nt 3' from the start codon. In this region, search for the following sequences: AA(N19)TT or AA(N21), where N=any nucleotide. The GC content of the selected sequence should be from about 30% to about 70%, preferably about 50%. To maximize the specificity of the RNAi, it may be desirable to use the selected sequence in a search for related sequences in the genome of interest; sequences absent from other genes are preferred. The secondary structure of the target mRNA may be determined or predicted, and it may be preferable to select a region of the mRNA that has little or no secondary structure, but it should be noted that secondary structure seems to have little impact on RNAi. When possible, sequences that bind transcription and/or translation factors should be avoided, as they might competitively inhibit the binding of a siRNA, sbRNA or stRNA (as well as other antisense oligonucleotides) to the mRNA.

Further general information about the design and use of siRNA may be found in "The siRNA User Guide," available at The Max-Planck-Institut fur Biophysikalishe Chemie website (http://www.mpibpc.mpg.de).

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. siRNA's having single nucleotide specificity can be designed as follows:

RNA may be produced enzymatically or by partial/total organic synthesis, any modified ribonucleotide can be introduced by in vitro enzymatic or organic synthesis. In one embodiment, an siRNA is prepared chemically. Methods of synthesizing RNA molecules are known in the art, in particular, the chemical synthesis methods as de scribed in Verma and Eckstein (1998) Annul Rev. Biochem. 67:99-134. In another embodiment, an siRNA is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

The siRNA molecules of the invention can be chemically synthesized, or can be transcribed in-vitro from a DNA template, or in-vivo from e.g., shRNA, or, by using recombinant human DICER enzyme, to cleave in-vitro transcribed dsRNA templates into pools of 20-, 21- or 23-bp duplex RNA mediating RNAi. The siRNA molecules can be designed using any method known in the art.

Nucleic acids can be synthesized in vitro, prepared from natural biological sources (e.g., cells, organelles, viruses and the like), or collected as an environmental or other sample. Examples of nucleic acids include without limitation oligonucleotides (including but not limited to antisense oligonucleotides), ribozymes, aptamers, polynucleotides, artificial chromosomes, cloning vectors and constructs, expression vectors and constructs, gene therapy vectors and constructs, PNA (peptide nucleic acid) DNA and RNA.

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl (2002), supra).

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis)

generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25): 14428-33. Epub 2001 Nov. 27).

The siRNA molecules of the present invention can comprise the sequences including, SEQ ID NO.: 5, e.g., GenBank accession No. NM_001904; TATGGGAACAATTGAAGTAAA (16A-1) (SEQ ID NO.: 1); CAGAAAGTGCCTGACACACTA (16A-2) (SEQ ID NO.:2); CTCGGGATGTTCACAACCGAA (16A+16B-1) (SEQ ID NO.:3); ATGGGTAGGGTAAATCAGTAA (16A+16B-2) (SEQ ID NO.:4); or fragments or variants of any one of SEQ ID NO.: 1, SEQ ID NO.: 2, SEQ ID NO.: 3, SEQ ID NO.: 4 or SEQ ID NO.: 5.

Methods of Determining the Proportion, Level, or Cellular Localization of CTNNB1-related Transcripts and Proteins A variety of techniques are available to carry out the methods of the invention. These techniques include, but are not limited to immunohistochemistry and polymerase chain reaction (PCR). Immunohistochemistry techniques can be used to measure the proportion, level or cellular localization of CTNNB1-related proteins in the methods described in this application. Such immunohistochemistry methods are particularly suited to measuring the cellular localization of CTNNB1-related proteins. Immunohistochemistry techniques are well known to those having ordinary skill in the art.

Figure 7:
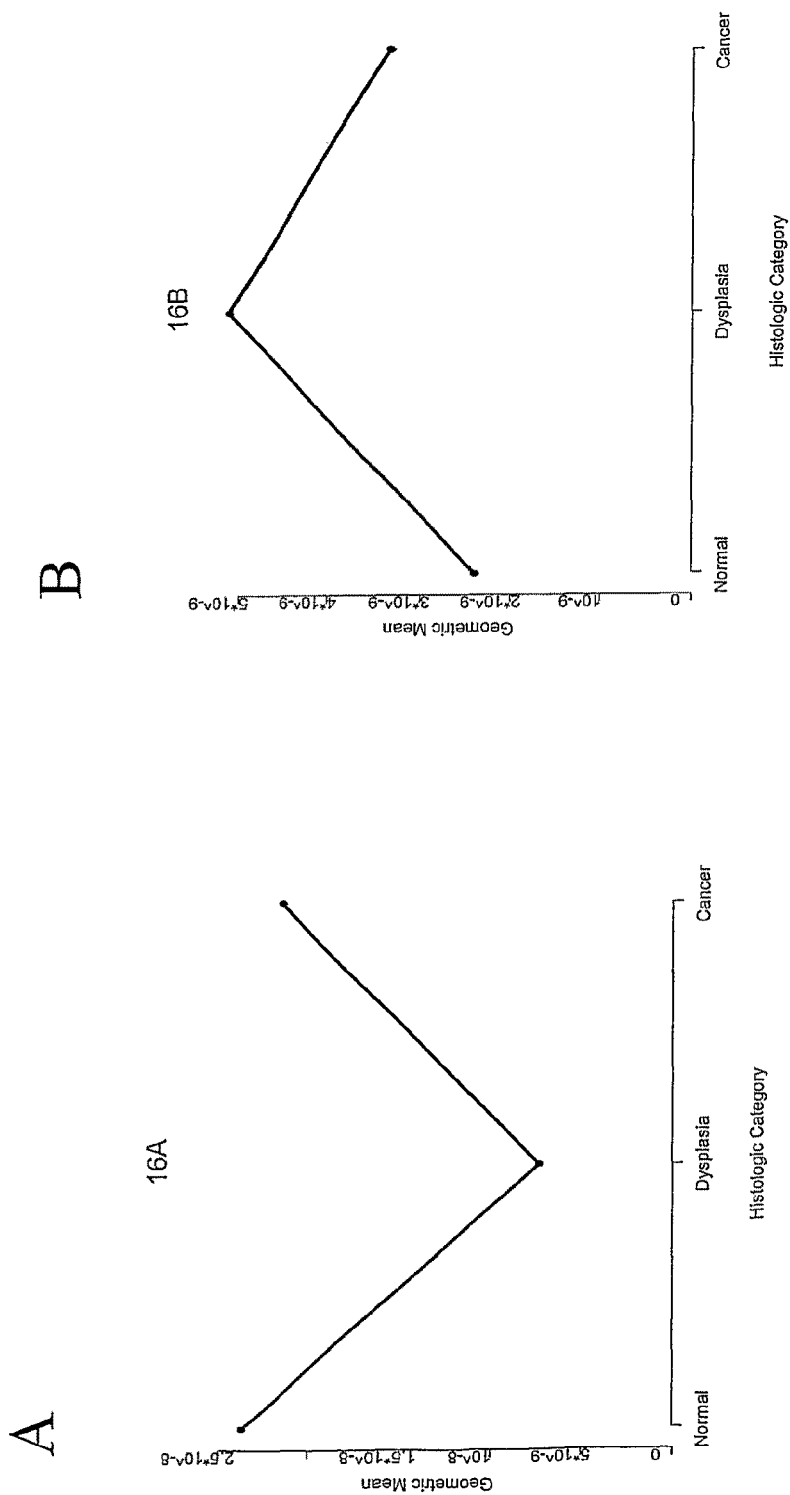
Figure 7:
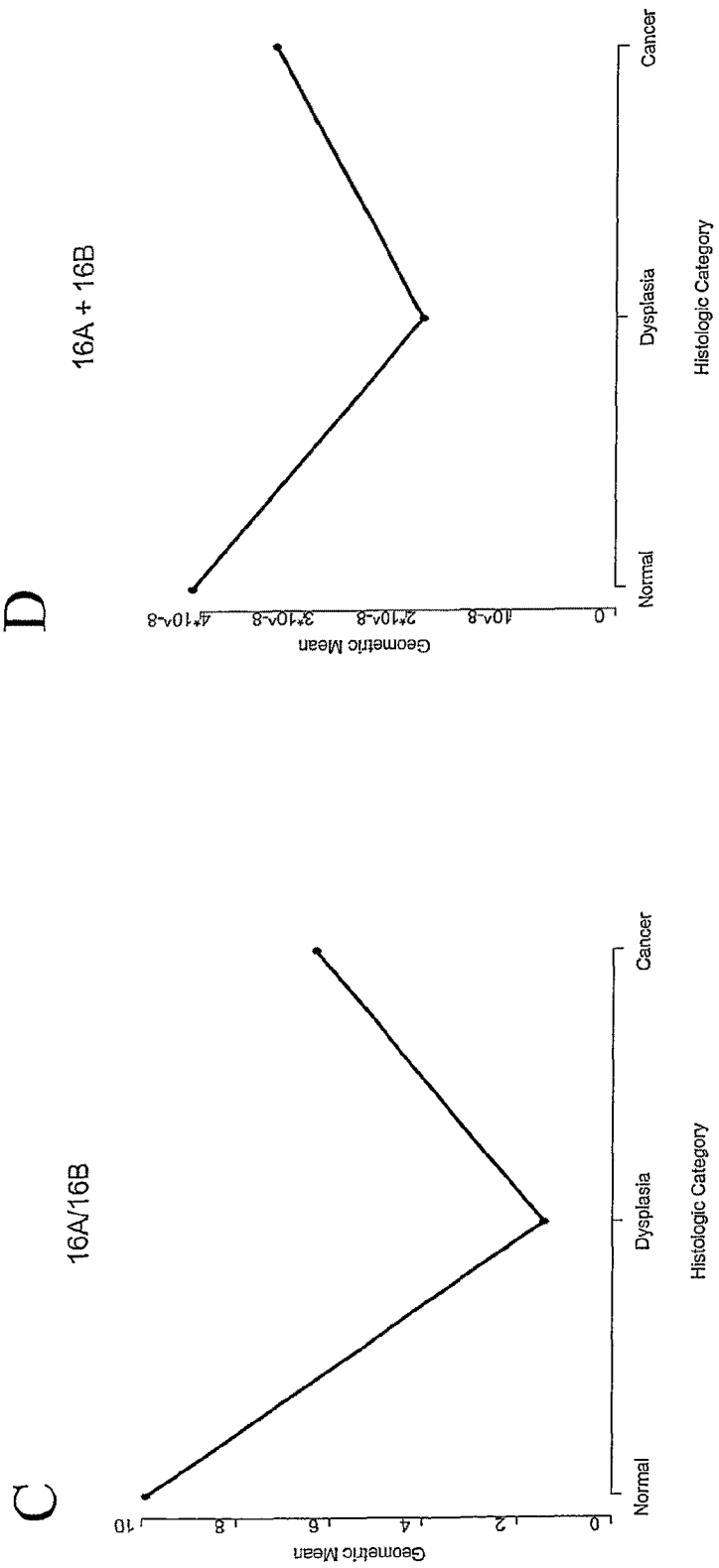
Figure 7:
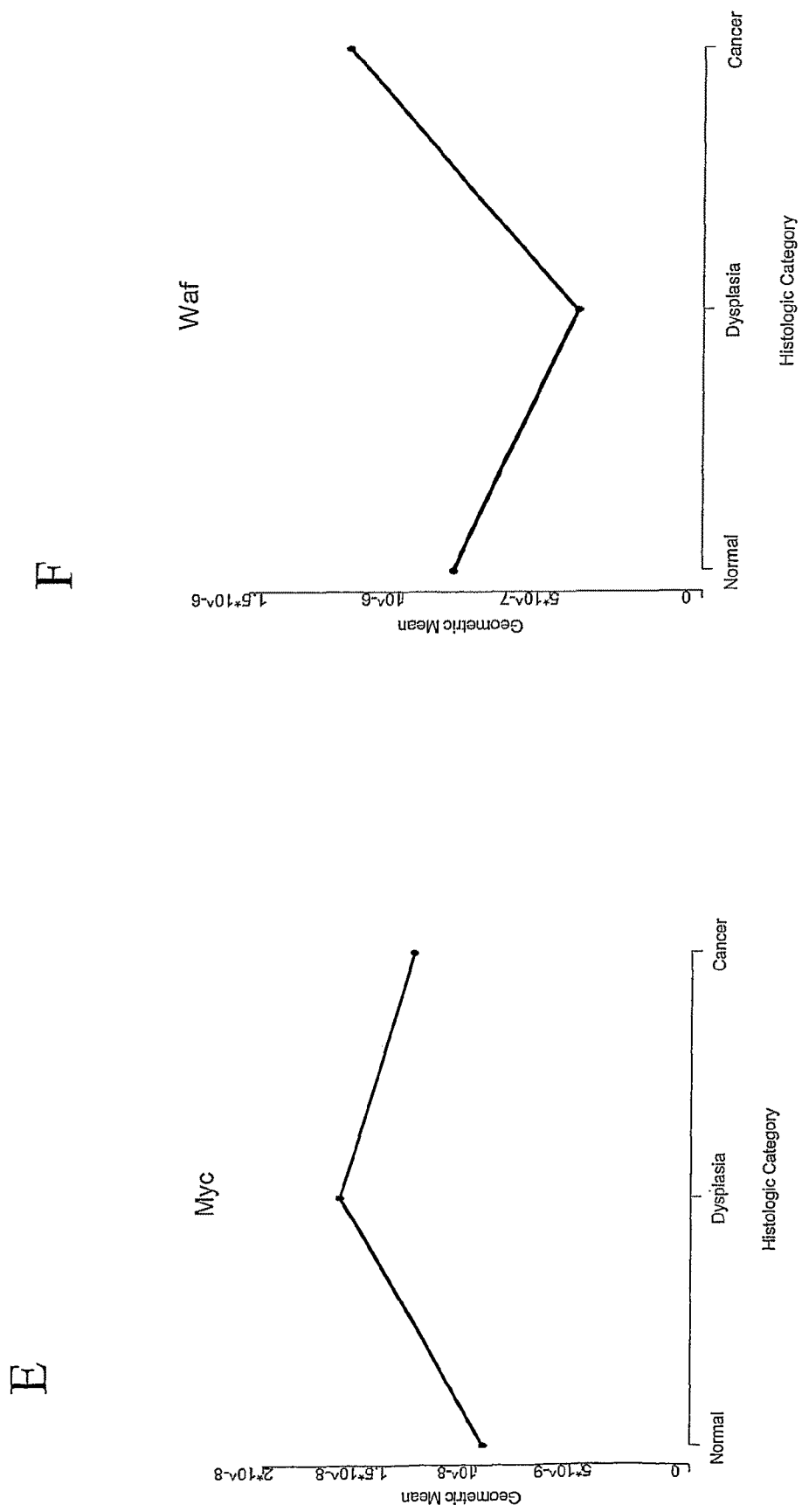
Figure 7:
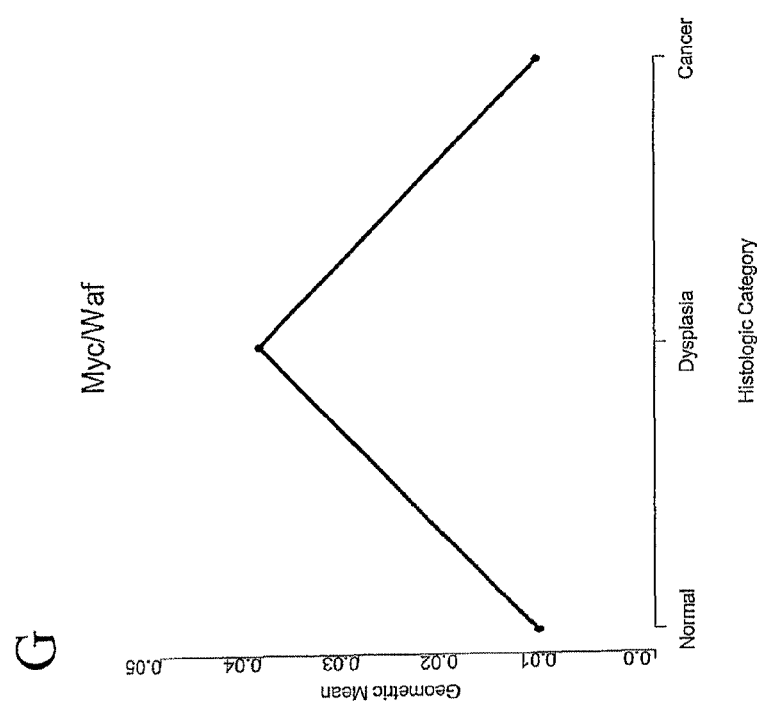

Some of the techniques which can be used to measure the proportion, level or cellular localization of CTNNB1-related transcripts in the methods of this invention employ PCR. A particularly useful technique for measuring the levels, proportions or cellular localization of CTNNB1-related transcripts is RT-PCR. PCR techniques utilize primers as a key reagent. Examples of some preferred primers useful in carrying out the methods of the claimed invention are found in FIG. 7. However, the invention is not limited by the PCR primers shown in FIG. 7 and other primers may be readily designed by one of ordinary skill in the art.

The method may further comprise reporting the proportion, level, cellular localization, activity, or correlations thereof to the subject or a health care professional. This may be done as "raw" results that have not been correlated, e.g., as a report of just the determined parameters, or it may be a correlated result.

When determining the levels of transcripts, the transcripts may have the published sequences, or they may be substantially identical to the published sequences due to polymorphisms or mutations.

The parameter, e.g., the proportions, levels, or cellular localization, may be determined by immunohistochemical methods. Methods for detecting the level of the protein may include extracting the protein contents of the cells, or extracting fragments of protein from the membranes of the cells, or from the cytosol, for example, by lysis, digestive, separation, fractionation and purification techniques, and separating the proteinaceous contents of the cells (either the crude contents or the purified contents) on a western blot, and then detecting the presence of the protein, or protein fragment by various identification techniques known in the art. For example, the contents separated on a gel may be identified by using suitable molecular weight markers together with a protein identification technique, or using suitable detecting moieties (such as labeled antibodies, labeled lectins, labeled binding agents (agonists, antagonists, substrates, co-factors, ATP, etc.). The level of protein on the western blot may be normalized to a total protein level of the cancer cell or to a standard internal protein, such as actin and/or GAPDH. The detection may also be by in situ, e.g., in the full tissue sample, by binding of specific recognition agents, to the biological markers when present in intact cells or in tissue. The presence of the labeled recognition moieties may be detected using techniques suited for the nature of the label. Where the recognition agents are fluorescent-labeled, the detection may be carried out by using a confocal microscope and directly viewing the level of the label bound (to the membranes). Where the recognition agents are labeled, for example, radio-labeled, the level may be determined by the determination of the radio-label level in the cells.

The determination of an expression level of a transcript may include, for example, the determination of the amount of RNA transcript for a particular protein or gene, or for a particular splice variant of the protein or gene. RNA levels may, for example, be detected by any methods used in the art for the detection of RNA, such as in situ hybridization with a detectable probe, for example, with a complementary sequence containing a detectable moiety (fluorescent, radioactive, chromatophoric moiety, etc). Various amplification methods sensitive enough to detect minute amounts of RNA are also useful. The parameters, e.g., the proportions, levels, or cellular localizations may be determined by PCR methods, such as RT-PCR, real time PCR, real time RT-PCR, sequencing, transcription assay, quantitative branched RNA analysis, in situ PCR, in situ RT-PCR, LCR (ligase chain reaction) and/or 3SR (self-sustained sequence replication). The amplification products may be identified by methods used in the art such as by separation on a gel and detection using a suitable labeled probe or by the optical unit of an RT PCR machine.

A sample may be tissue samples or cell from a subject or patient, for example, obtained by biopsy, intact cells, for example cells that have been separated from a tissue sample, or intact cells present in blood or other body fluid, cells or tissue samples obtained from the subject, including paraffin embedded tissue samples, proteins extracted obtained from a cell, cell membrane, nucleus or any other cellular component or mRNA obtained from the nucleus or cytosol. The sample may also be whole blood, or any portion of blood that has been separated from the whole blood sample. Samples may also be reference cells or a standard cell sample. For example, when referring to "detecting the presence or absence of a β-catenin gene (CTNNB1) related cancer in a sample," the sample may be from a subject (e.g., biopsy, blood, and the like) or from a reference cell or standard cell, such as a cell line (e.g., primary cell line or established cell line).

Where the level of the tested parameter is localization in various cellular components, the amount of the marker in each compartment, or ratio of the amounts in various components may be determined. This may be done, for example, by separating the cellular components (for example lysing the cell and obtaining separately the membrane and the cytosol) or obtaining separately the cytosol and the nucleus and determining the protein content or RNA or transcript level of the relevant biological marker in each separated cellular components, by using any one of the methods mentioned above or other methods used to determine protein contents.

Alternatively it is possible to determine CTNNB1 localization by using labeled CTNNB1 binding agents (e.g., antibodies, agonists, antagonists) especially fluorescently labeled binding agents. Agonists and antagonists include agents that interact either directly or indirectly with CTNNB1, or that cause a change in the cellular localization or that change expression of CTNNB1 transcripts. It is possible to monitor the localization of CNNB1 in cells, for example, using microscopy.

In regard to the screening methods disclosed herein, in general, a physiological parameter (e.g., level, proportion or cellular localization) may change in a manner as compared to a control (e.g., reference). For example, a change indicative of increased proliferation ("pro-proliferative") as a result of treatment such as administration of a drug (preferably a CTNNB1 modulator, most preferably a CTNNB1 agonist), or a change indicative of decreased proliferation ("anti-proliferative") as a result of treatment, such as administration of the drug.

In cancers, as compared with normal cells, the expression level of:
16A decreases,
16B increases,
cMyc increases, and/or
Waf1 decreases.
Thus, the ratio of 16A/16B decreases and the ratio of Myc/Waf increases.
A therapeutic response would be illustrated by changes in the opposite direction. During treatment of a cancerous cell, a treatment response may include the expression level of:
16A increasing,
16B decreasing,
cMyc decreasing, and/or
Waf increasing.
Thus, the ratio of 16A/16B would increase and the ratio of Myc/Waf would decrease.

Examples indicative of anti-proliferative effect, potential, or efficacy of a treatment include: Examples indicating diagnosis or prognosis of a CTNNB1 related disease include:
 a decrease in the proportion of 16A transcript to 16B transcript indicates that the subject may have a CTNNB1 related cancer, preneoplastic lesion, or be at increased risk for developing cancer;
 an increase in the proportion of cMYC transcript to WAF1 transcript indicates that the subject may have a CTNNB1 related cancer, a preneoplastic lesion, or at increased risk for developing cancer or preneoplastic disease;
 a decrease in the level of the 16A transcript or in the WAF1 transcript indicates that the subject may have a CTNNB1 related cancer, or at increased risk for developing cancer or preneoplastic disease; and/or
 an increase in one or more of the levels of 16B transcript, cMYC transcript or the level of overall transcription activity indicates that the subject may have a CTNNB1 related cancer, or at increased risk for developing cancer or preneoplastic disease.

Changes indicative of pro-proliferative effects of the treatment include:
 a decrease in the proportion of 16A transcript to 16B transcript indicates that the subject may have a CTNNB1 related cancer, preneoplastic lesion, or be at increased risk for developing cancer;
 an increase in the proportion of cMYC transcript to WAF1 transcript indicates that the subject may have a CTNNB1 related cancer, a preneoplastic lesion, or at increased risk for developing cancer or preneoplastic disease;
 a decrease in one or more of the levels of the 16A transcript or the WAF1 transcript indicates that the subject may have a CTNNB1 related cancer, or at increased risk for developing cancer or preneoplastic disease; and/or
 an increase in one or more of the levels of 16B transcript, cMYC transcript or the level of overall transcription activity indicates that the subject may have a CTNNB1 related cancer, or at increased risk for developing cancer or preneoplastic disease.

The changes indicative of a decreased proliferation show effectiveness of a CTNNB1 modulator, preferably a CTNNB1 agonist, administered for the treatment of a disease state wherein a CTNNB1 therapeutically beneficial effect may be evident by decrease or inhibition of proliferation. Examples of such diseases that are typically characterized by excess proliferation include, without being limited thereto, all types of cancer; and, in particular, all types of solid tumors; skin proliferative diseases (e.g., psoriasis); a variety of benign hyperplastic disorders; and inflammatory diseases.

Methods of identifying a tumor that responds include determining whether there is a decrease in the proportion of 16A transcript to 16B transcript indicates that the subject may have a CTNNB1 related cancer, preneoplastic lesion, or be at increased risk for developing cancer; an increase in the proportion of cMYC transcript to WAF1 transcript indicates that the subject may have a CTNNB1 related cancer, a preneoplastic lesion, or at increased risk for developing cancer or preneoplastic disease; a decrease in the level of the 16A transcript or a decrease in the WAF1 transcript indicates that the subject may have a CTNNB1 related cancer, or at increased risk for developing cancer or preneoplastic disease; and/or an increase in one or more of the levels of 16B transcript, cMYC transcript or the level of overall transcription activity indicates that the subject may have a CTNNB1 related cancer, or at increased risk for developing cancer or preneoplastic disease.

It has been shown in accordance with the invention that increased expression of CTNNB1 can be found not only in the primary tumor site but also in metastasis thereof.

Where the disease is cancer the cells that are obtained from the subject may be cells suspected of being transformed as well as other cells notably blood cells such as neutrophils. Cells suspected of being transformed may be obtained by methods known for obtaining "suspicious" cells such as by biopsy, needle biopsy, fine needle aspiration, swabbing, surgical excision, and other techniques known in the art. The diagnosis of a disease or disease state may be by self-diagnosis, or by diagnosis by a health care professional. The health care professional may use any method known in the art to diagnose a disease, for example, medical history of the subject and/or family, as well as physical exam and various imaging (NMR, MR, scanning, ultrasound, mammography) or pathological techniques.

Changes in parameters (e.g., levels of protein or RNA expression, cellular localizations of proteins, and/or proportions or ratios of levels of protein and/or RNA expression or nuclear localization) indicative of an increased proliferation, a pathological progression toward cancer, a β-catenin gene (CTNNB1) related cancer, a tumor that responds to a CTNNB1 related directed therapy, a suitable subject with cancer, preneoplasia, and/or at increased cancer risk, demonstrate that treatment with a CTNNB1 related cancer therapy would be efficacious. Such changes include:
 a decrease in the proportion of 16A transcript to 16B transcript indicates that the subject may have a CTNNB1 related cancer, preneoplastic lesion, or be at increased risk for developing cancer;
 an increase in the proportion of cMYC transcript to WAF1 transcript indicates that the subject may have a CTNNB1 related cancer, a preneoplastic lesion, or at increased risk for developing cancer or preneoplastic disease;

a decrease in the level of the 16A transcript or in the WAF1 transcript indicates that the subject may have a CTNNB1 related cancer, or at increased risk for developing cancer or preneoplastic disease; and/or an increase in one or more of the levels of 16B transcript, cMYC transcript or the level of overall transcription activity indicates that the subject may have a CTNNB1 related cancer, or at increased risk for developing cancer or preneoplastic disease.

Changes in parameters (e.g., levels of protein or RNA expression, cellular localizations of proteins, and/or proportions or ratios of levels of protein and/or RNA expression or nuclear localization) are useful for identifying CTNNB1 related cancer CTNNB1 therapeutics, and for predicting a β-catenin gene (CTNNB1) related cancer, neoplasia, or preneoplasia.

Monitoring the levels, ratios, or cellular localization of at least one physiological parameter of the biological marker in the cells, in accordance with one of the uses of the above method, may also help to screen for likely candidates for treatment of disease states related to CTNNB1.

For example, it is possible to use cell cultures of tissue samples, for example, a specific line of cancer cells derived from a type of cancer that is the intended target for therapy. Determination of modulation of one or more of the physiological parameters before, during, and/or after treatment with a drug candidate compound may serve as an indication for possible use of the drug candidate in treating the CTNNB1 related disease state.

The term diagnosis as used herein generally comprises any kind of assessment of the presence of absence of a medically relevant condition. Diagnosis thus comprises processes such as screening for the predisposition for a medically relevant condition, screening for the precursor of a medically relevant condition, screening for a medically relevant condition, clinical or pathological diagnosis of a medically relevant condition, etc. Diagnosis of medically relevant conditions as used herein may comprise examination of any condition, that is detectable on a cytological, histological, biochemical or molecular biological level that may be useful in respect to the human health and/or body. Such examinations may comprise e.g. medical diagnostic methods and research studies in life sciences. In one embodiment of the invention, the method is used for diagnosis of medically relevant conditions such as e.g. diseases. Such diseases may for example comprise disorders characterized by proliferation of cells or tissues.

In one embodiment, the diagnosis pertains to diagnosis of cancers and their precursory stages, to monitoring of the disease course in cancers, to assessment of prognosis in cancers and to detection of disseminated tumor cells, e.g., in the course of minimal residual disease diagnosis. The methods according to the present invention may for example be used in the course of clinical or pathological diagnosis of cancers and their precursory stages or in routine screening tests as performed for particular cancers such as for example for examination of swabs e.g. in screening tests for cervical lesions, of bronchial lavages or brushes for lung cancer, of esophageal balloon screening for esophageal cancer or of stool for lesions of the gastrointestinal tract, e.g. colorectal lesions.

One aspect of this normalization includes comparing the results of a determination of one or more of the parameters disclosed herein and determining one or more of the following:

a decrease in the proportion of 16A transcript to 16B transcript indicates that the subject may have a CTNNB1 related cancer, preneoplastic lesion, or be at increased risk for developing cancer;

an increase in the proportion of cMYC transcript to WAF1 transcript indicates that the subject may have a CTNNB1 related cancer, a preneoplastic lesion, or at increased risk for developing cancer or preneoplastic disease;

a decrease in the level of the 16A transcript or in the WAF1 transcript indicates that the subject may have a CTNNB1 related cancer, or at increased risk for developing cancer or preneoplastic disease; and/or an increase in one or more of the levels of 16B transcript, cMYC transcript or the level of overall transcription activity indicates that the subject may have a CTNNB1 related cancer, or at increased risk for developing cancer or preneoplastic disease.

"Correlating" may also comprise for example, determining one or more of the following:

a decrease in the proportion of 16A transcript to 16B transcript indicates that the subject may have a CTNNB1 related cancer, preneoplastic lesion, or be at increased risk for developing cancer;

an increase in the proportion of cMYC transcript to WAF1 transcript indicates that the subject may have a CTNNB1 related cancer, a preneoplastic lesion, or at increased risk for developing cancer or preneoplastic disease;

a decrease in the level of the 16A transcript or in the WAF1 transcript indicates that the subject may have a CTNNB1 related cancer, or at increased risk for developing cancer or preneoplastic disease; and/or an increase in one or more of the levels of 16B transcript, cMYC transcript or the level of overall transcription activity indicates that the subject may have a CTNNB1 related cancer, or at increased risk for developing cancer or preneoplastic disease.

Correlating may include making an assessment that a particular result is not accurate. Correlating may also include predicting whether a certain level, proportion, or cellular localization is a meaningful in the context of diagnosis, prognosis, and/or monitoring of treatment. Correlating may be done by mathematical formulae, computer program, or a person. As disclosed herein, certain levels, proportions, and/or cellular localizations are predictive of disease state or progression of disease state. Correlating or normalization, especially in the context of a diagnosis, may also include or take into consideration, such factors as, the total number of cells present in the sample, of the presence or absence of a particular cell type or types in a sample, the presence or absence of an organism or of cells of an organism in a sample, the number of cells of a particular cell type or organism present in the sample, the proliferative characteristics of cells present in the sample, or the differentiation pattern of the cells present in the sample.

In certain embodiments normalization may also comprise demonstrating the adequacy of the test, wherein as the case may be inadequate test results may be discarded or classified as invalid. Therefore normalization as used in the context of the present invention may comprise qualitative or semi-quantitative methods for normalization. In certain embodiments, semi-quantitative normalization may comprise determining a threshold value for a normalization marker.

In one embodiment, semi-quantitative normalization may be applied, e.g., as follows: the level determined for the relevant marker may be regarded as a valid test result if the level of the normalization marker exceeds a defined threshold value. In cases wherein the threshold value is not reached, the test result for the relevant marker is regarded as invalid and a diagnosis may not be assessed on the basis of the test. In other embodiments a threshold may be set that may not be exceeded. In certain embodiments, qualitative normalization may be performed with respect to the presence or absence of a normalization marker. In those cases, e.g. the value determined for the relevant marker is compared to the presence or absence of a normalization marker. As predefined, the value is valid only in case the normalization parameter (presence or absence of a detectable level of the normalization marker) is met.

The normalization or correlating may further comprise the detection of the presence, absence, or differentially localized or expressed component within a sample, and additionally the detection of the total level of a particular transcript of protein.

Therapeutic Candidates

Thus, the invention provides methods for identifying modulators, e.g., candidate or test compounds or agents (e.g. peptides, small molecules or other drugs) that have a stimulatory or inhibitory effect on the pathway(s) affected by the agent and have anti-proliferative properties. Such compounds may include, but are not limited to, peptides made of D- and/or L-configuration amino acids (in, for example, the form of random peptide libraries; (see e.g., Lam, et al., Nature, 354:82-4 (1991)), phosphopeptides (in, for example, the form of random or partially degenerate, directed phosphopeptide libraries; see, e.g., Songyang, et al., Cell, 72:767-78 (1993)), antibodies, siRNA molecules, and small organic or inorganic molecules. Compounds identified may be useful, for example, in modulating the activity of β-catenin pathway target gene proteins, preferably mutant proteins; elaborating the biological function of the β-catenin pathway target gene protein; or screening for compounds that disrupt normal β-catenin pathway target gene interactions or themselves disrupt such interactions.

In one embodiment, the invention provides libraries of test compounds. The test compounds of the present invention can be obtained using any of the numerous approaches in combinatorial library methods known in the art, including: biological libraries, spatially addressable parallel solid phase or solution phase libraries; synthetic library methods requiring deconvolution; the one-bead one-compound library method; and synthetic library methods using affinity chromatography selection. The biological library approach is exemplified by peptide libraries, while the other four approaches are applicable to peptide, non-peptide oligomer or small molecule libraries of compounds (Lam, K. S. (1997) "Application of combinatorial library methods in cancer research and drug discovery." Anticancer Drug Des. 12:145).

Methods for the synthesis of molecular libraries can be found in the art, for example, in (i) De Witt, S. H. et al. (1993) "Diversomers: an approach to nonpeptide, nonoligomeric chemical diversity." PNAS 90:6909, (ii) Erb, E. et al. (1994) "Recursive deconvolution of combinatorial chemical libraries." PNAS 91:11422, (iii) Zuckermann, R. N. et al. (1994) "Discovery of nanomolar ligands for 7-transmembrane G-protein-coupled receptors from a diverse N-(substituted) glycine peptoid library." J. Med Chem. 37: 2678 and (iv) Cho, C. Y. et al. (1993) "An unnatural biopolymer." Science 261: 1303. Libraries of compounds may be presented in i) solution (e.g. Houghten, R. A. (1992) "The use of synthetic peptide combinatorial libraries for the identification of bioactive peptides." BioTechniques 13:412) ii) on beads (Lam, K. S. (1991) "A new type of synthetic peptide library for identifying ligand-binding activity." Nature 354:82), iii) chips (Fodor, S. P. (1993) "Multiplexed biochemical assays with biological chips." Nature 364:555), iv) bacteria (U.S. Pat. No. 5,223,409), v) spores (U.S. Pat. Nos. 5,571,698, 5,403,484, and 5,223,409), vi) plasmids (Cull, M. G. et al. (1992) "Screening for receptor ligands using large libraries of peptides linked to the C terminus of the lac repressor." PNAS 89:1865) or vii) phage (Scott, J. K. and Smith, G. P. (1990) "Searching for peptide ligands with an epitope library." Science 249: 386)

Compounds that may be co-administered with a CTNNB1 directed therapy include, anti-bacterial, anti-fungal, anti-viral, anti-hypertension, anti-depression, anti-anxiety, and anti-arthritis substances, as well as substances for the treatment of allergies, diabetes, hypercholesteremia, osteoporosis, Alzheimer's disease, Parlinson's disease, and/or other neurodegenerative diseases, and obesity. Specific categories of test substances can include, but are not limited to, PPAR agonists, HIV protease inhibitors, anti-inflammatory drugs, estrogenic drugs, anti-estrogenic drugs, antihistamines, muscle relaxants, anti-anxiety drugs, anti-psychotic drugs, and anti-angina drugs. Other drugs may be co-administered with CTNNB1 related therapies according to the needs of a particular subject.

Anti-inflammatory drugs include, for example, inflammatory agent, including, non-steroidal agents and COX-2 specific agents, e.g., Diclofenac, Diflunisal, Etodolac, Fenoprofen, Flurbiprofen, Ibuprofen, Indomethacin, Ketoprofen, Ketorolac, Meclofenamate, Mefenamic Acid, Nabumetone, Naproxen, Oxaprozin, Piroxicam, Sulindac, Tolmetin, and related substances.

Examples of muscle relaxants include Dantrolene (e.g., Dantrium®), Baclofen (e.g., Lioresal®), Carisoprodol (e.g., Soma®), Chlorphenesin (e.g., Maolate®), Chlorzoxazone (e.g., Paraflex®), Cisatracurium, Cyclobenzaprine (e.g., Flexeril®), Dantrolene, Diazepam (e.g., Valium®), Metaxalone (e.g., Skelaxin®), Gallamine, Methocarbamol (e.g., Robaxin®), Mivacurium, Orphenadrine (e.g., Norflex®), Pancuronium, Rocuronium, Tizanidine, Suxamethonium, Vecuronium, and related substances.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In *Molecular Cloning: A Laboratory Manual* (1982); *DNA Cloning: A Practical Approach*, Volumes I and II, D. N. Glover, ed., (1985); *Oligonucleotide Synthesis*, M. J. Gait, ed., (1984); Ausubel, et al., (eds.), *Current Protocols In Molecular Biology*, John Wiley & Sons, New York, N.Y. (1993); *Nucleic Acid Hybridization*, B. D. Hames & S. J. Higgins, eds., (1985); *Transcription and Translation*, B. D. Hames & S. I. Higgins, eds., (1984); *Animal Cell Culture*, R. I. Freshney, ed. (1986); and B. Perbal, *A Practical Guide to Molecular Cloning* (1984).

Methods of Treatment, Management or Prevention

One embodiment of this invention is directed to a method of treating or managing cancer comprising administering to a patient in need of such treatment or management a therapeutically or prophylactically effective amount of a compound that inhibits the synthesis or expression of the CTNNB1 gene.

As used herein, and unless otherwise indicated, the term "treating cancer" or "treatment of cancer" means to inhibit the replication of cancer cells, inhibit the spread of cancer, decrease tumor size, lessen or reduce the number of cancerous cells in the body, or ameliorate or alleviate the symptoms of the disease caused by the cancer. The treatment is considered therapeutic if there is a decrease in mortality and/or morbidity, or a decrease in disease burden manifest by reduced numbers of malignant cells in the body.

As used herein, and unless otherwise indicated, the term "preventing cancer" or "prevention of cancer" means to prevent the occurrence or recurrence of the disease state of cancer. As such, a treatment that impedes, inhibits, or interferes with metastasis, tumor growth, or cancer proliferation has preventive activity. Preventing cancer, as used herein, does not require that a cancer never occur but, is used, for example, in the context of delaying the onset of the appearance of a malignant state when a benign hyperplastic state has been identified or delaying the recurrence of the appearance of a tumor or recurring tumor growth after arrest of growth following treatment, or delaying metastasis of a tumor.

As used herein, and unless otherwise indicated, the term "managing" encompasses preventing the recurrence of cancer in a patient who had suffered from cancer, lengthening the time a patient who had suffered from cancer remains in remission, preventing the occurrence of cancer in patients at risk of suffering from cancer (e.g., patients who had been exposed to high amounts of radiation or carcinogenic materials, such as asbestos; patients infected with viruses associated with the occurrence of cancer, such as, but not limited to, HIV and Kaposi's sarcoma-associated herpesvirus; and patients with genetic predispositions to cancer, such as those suffering from Downs syndrome), and preventing the occurrence of malignant cancer in patients suffering from pre-malignant or non-malignant cancers.

Prophylactic Methods

In one aspect, the invention provides a method for preventing in a subject, a disease or condition associated with an aberrant or unwanted target gene expression or activity, by administering to the subject a therapeutic agent (e.g., a siRNA or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., a siRNA or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Methods of the invention can be used to treat and manage patients suffering from primary and metastatic cancer. They further encompass methods of treating patients who have been previously treated for cancer, as well as those who have not previously been treated for cancer. The invention encompasses first-line, second-line, third-line and further lines cancer treatments.

It would be readily apparent to one of ordinary skill in the art that the compositions of this invention (e.g., antisense oligonucleotides, siRNAs, and other agents described herein) of this invention can be combined with one or more of other anti-cancer therapies. The compositions of this invention can be administered simultaneously or sequentially with antineoplastic agents such as antimetabolites, alkylating agents, spindle poisons and/or intercalating agents, and proteins such as interferons.

Examples of particular second anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracycline; anthramycin; aromatase inhibitors; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; chlorodeoxyadenosine; cirolemycin; cisplatin; cladribine; corticosteroids; crisnatol mesylate; cyclophosphamide; cytarabine; cytosine arabinose; dacarbazine; dactinomycin; daunorubicin hydrochloride; decitabine; deoxyconformycin; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamnitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; folinic acid; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; leucovorin; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; myelopurine; navelbine; nitrosoureas camustine; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; progestins; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; taxane; tecogalan sodium; tegafur; teloxantrone hydrochloride; temoporfin; teniposide; teroxirone; testolactone; thiamiprine; thioguanine; thiotepa; tiazofurin; tirapazamine; topoisomerase inhibitors; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Still other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard second anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonennin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urolinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The determination of the identity and amount of second anti-cancer agent(s) for use in a method of the invention can be readily made by ordinarily skilled medical practitioners using standard techniques known in the art, and will vary depending on the type and severity of cancer being treated.

The compositions of this invention and second anti-cancer agents can be administered simultaneously or sequentially by the same or different routes of administration. The suitability of a particular route of administration employed for a particular compound will depend on the compound itself (e.g., whether it can be administered orally without decomposing prior to entering the blood stream) and the disease being treated. For example, treatment of tumors on the skin or on exposed mucosal tissue may be more effective if one or both active ingredients are administered topically, transdermally or mucosally (e.g., by nasal, sublingual, buccal, rectal, or vaginal administration). Treatment of tumors within the body, or prevention of cancers that may spread from one part of the body to another, may be more effective if one or both of the active ingredients are administered parenterally or orally. Similarly, parenteral administration may be preferred for the acute treatment of a disease, whereas transdermal or subcutaneous routes of administration may be employed for chronic treatment or prevention of a disease. Preferred routes of administration for the anti-cancer agents are known to those of ordinary skill in the art.

Pharmaceutical Compositions

The present invention also provides pharmaceutical compositions. Such compositions comprise a therapeutically effective amount of a CTNNB1 therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the CTNNB1 therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water can be a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the CTNNB1 therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The CTNNB1 therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

Preferred pharmaceutical compositions and dosage forms comprise a CTNNB1 therapeutic of the invention, or a pharmaceutically acceptable prodrug, salt, solvate, or clathrate thereof, optionally in combination with one or more additional active agents.

The amount of the CTNNB1 therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1-50 milligrams of active compound per kilogram body weight. Suitable dosage ranges for intranasal administration are generally about 0.1 mg/kg body weight to 50 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

For antibodies, proteins, polypeptides, peptides and fusion proteins encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

The CTNNB1 therapeutics of the present invention may also be administered by controlled release means or delivery devices that are well known to those of ordinary skill in the art, such as those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566. These controlled release compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art may be readily selected for use with the pharmaceutical compositions of the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include extended activity of the drug, reduced dosage frequency, and/or increased patient compliance.

Most controlled-release formulations are designed to initially release an amount of the CTNNB1 therapeutic that promptly produces the desired CTNNB1 therapeutic effect, and gradually and continually releases other amounts of the CTNNB1 therapeutic to maintain the appropriate level of CTNNB1 therapeutic effect over an extended period of time. In order to maintain this constant level of CTNNB1 therapeutic in the body, the CTNNB1 therapeutic must be released from the composition at a rate that will replace the amount of CTNNB1 therapeutic being metabolized and excreted from the body. The controlled-release of the CTNNB1 therapeutic may be stimulated by various inducers, for example, pH, temperature, enzymes, water, or other physiological conditions or compounds. Such controlled-release components in the context of the present invention include, but are not limited to, polymers, polymer matrices, gels, permeable membranes, liposomes, microspheres, or the like, or a combination thereof, that facilitates the controlled-release of the active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The other CTNNB1 therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NTHEs, see Paul A. Insel, *Analgesic-Antipyretic and Antiinflammatory Agents and Drugs Employed in the Treatment of Gout*, in Goodman & Gilman's *The Pharmacological Basis of CTNNB1 therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Other Examples of prophylactic and CTNNB1 therapeutic agents include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

In combination therapy treatment, both the compounds of this invention and the other drug agent(s) are administered to mammals (e.g., humans, male or female) by conventional methods. The agents may be administered in a single dosage form or in separate dosage forms. Effective amounts of the other CTNNB1 therapeutic agents are well known to those skilled in the art. However, it is well within the skilled artisan's purview to determine the other CTNNB1 therapeutic agent's optimal effective-amount range. In one embodiment of the invention where another CTNNB1 therapeutic agent is administered to an animal, the effective amount of the compound of this invention is less than its effective amount would be where the other CTNNB1 therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In various embodiments, the therapies (e.g., prophylactic or CTNNB1 therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, one or more compounds of the invention and one or more other therapies (e.g., prophylactic or CTNNB1 therapeutic agents) are cyclically administered. Cycling therapy involves the administration of a first therapy (e.g., a first prophylactic or CTNNB1 therapeutic agent) for a period of time, followed by the administration of a second therapy (e.g. a second prophylactic or CTNNB1 therapeutic agent) for a period of time, optionally, followed by the administration of a third therapy (e.g., prophylactic or CTNNB1 therapeutic agent) for a period of time and so forth, and repeating this sequential administration, e.g., the cycle in order to reduce the development of resistance to one of the therapies, to avoid or reduce the side effects of one of the therapies, and/or to improve the efficacy of the therapies.

In certain embodiments, the administration of the same compounds of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or CTNNB1 therapeutic agent) other than a compound of the invention may be repeated and the administration may be separated by at least at least 1 day, 2 days, 3 days, 5 days, 10 days, 15 days, 30 days, 45 days, 2 months, 75 days, 3 months, or at least 6 months.

EXAMPLES

It should be appreciated that the invention should not be construed to be limited to the examples which are now described; rather, the invention should be construed to include any and all applications provided herein and all equivalent variations within the skill of the ordinary artisan.

Example 1

Real Time RT-PCR Analysis

Resection specimens from six patients were fully submitted in histology cassettes and stored at −70 degrees C. until Real Time RT-PCR analysis of CTNNB1, MYC and WAF1.

Serial 5-micron frozen sections were cut from each histology cassette and representative foci of normal (N=11), low grade dysplasia (N=11), high grade dysplasia (N=8), carcinoma in-situ (N=4), and invasive squamous cell carcinoma (N=11) from the six fully submitted esophageal resections were chosen based on histologic review by a pathologist (MR) of corresponding hematoxylin and eosin stained slides using accepted histologic criteria. RNA was isolated from laser capture microdissected tissue foci using a standard Trizol extraction protocol in the presence of yeast carrier tRNA. Approximately 25% of the resultant RNA was used from each LCM sample for the synthesis of cDNA. Using the Thermoscript RT-PCR Synthesis (Invitrogen) System, oligo dT and random hexamer primers were employed to synthesize cDNA following the manufacturer's protocol. Primers specific for the 16A and 16B isotypes of CTNNB1, c-MYC, p21 (Waf1), GAPDH, 18s rRNA and B-Actin (FIG. 8) were used to amplify specific products either with SYBR green (50 cycles—Real Time RT-PCR) or without SYBR green (35 cycles conventional gel-based RT-PCR). Primers useful in the invention are as shown in FIG. 8. Unless specified, all reaction conditions were conducted in Platinum Supermix (Invitrogen) using standard PCR conditions including a reannealing temperature of 55° C. For standardizing Real Time PCR product concentrations, purified inserts of the appropriate products were used in serial dilutions and then plotted on a log-scale to calculate starting quantity (threshold starting cycle). All samples were normalized to housekeeping controls (B-actin) prior to calculating levels of gene expression.

Example 2

Characterization of Exon 3 Mutations

The frequency of exon 3 CTNNB1 mutations was characterized. It was demonstrated that there is a change frequently involved in or associated with dysregulation of the CTNNB1 gene. The expression of the CTNNB1 gene was compared with transcript variants and the expression of downstream targets such as MYC and WAF1 (p21) across the neoplastic progression of ESCCs from a high-risk region of China. Mutational analysis was performed on 56 tumors and corresponding germline (blood) DNA using primers to exon 3 of CTNNB1 and SSCP DNA sequencing gels. Quantitative Real Time RT-PCR was performed on 41 foci representing the histologic spectrum from normal to invasive cancer using specific primer sets for alternative splice variants that differ by the presence (16A) or absence (16B) of a 159-bp non-coding segment of exon 16 of CTNNB1, in conjunction with downstream targets MYC and WAF1. Two unique mutations were identified in two of the 56 cases, consisting of a serine to phenylalanine somatic substitution (S37F) in the SxxxS repeat region, and a germline polymorphism resulting in a threonine to alanine substitution (T59A). Thus, mutation of CTNNB1 exon 3 is a rare event in this population and, consequently, is unlikely to be etiologically associated with its high rates of ESCC. RT-PCR analysis successfully confirmed the presence of both β-catenin splice variants in histologically normal and preneoplastic squamous epithelium and invasive tumors of the esophagus, and identified a significant reduction in the 16A/16B ratio (p=0.014) and an accompanying significant increase in the c-MYC/WAF1 expression ratio (p=0.001) with progression from normal mucosa to dysplasia. The data in this example demonstrate that there are two CTNNB1 transcripts in histologically normal appearing esophageal squamous cells, squamous dysplasia and invasive ESCC. These results show an increase in the minor mRNA (16B) isoform and changes in the expression of downstream markers consistent with increased transcription during the histologic progression from normal to squamous dysplasia.

Exon 3 of CTNNB1 is infrequently mutated in ESCC tumors (2 out of 56 (4%) of ESSC cases) and we have identified a single somatic TCT-TTT change (S37F), resulting in a serine to phenylalanine substitution in the SxxxS repeat region, and a germline polymorphism ACC-GCC change (T59A) resulting in a threonine to alanine substitution. This finding of a low frequency of mutations is consistent with that observed by others in ESCC (De Castro Virchow's Arch 2000, Ninomiya Int J Cancer 2000) and histologically similar squamous cell cancers of the head and neck (Gonzalez's J Clin Pathol 1998). In this high-risk population, mutation of exon 3 does not seem to be responsible for the increase in protein expression identified in the majority of these esophageal tumors.

Six fully blocked frozen esophagectomy specimens, with an average of 7 (range 3 to 15) foci per specimen representing the histologic spectrum of neoplastic progression from normal to invasive squamous cell carcinoma were selected for RT-PCR analysis.

From these resections, a total of 11 foci of histologically normal (Nml) epithelium were found in 4 esophagectomies, 11 foci of low grade dysplasia (LGD) were found in 6 esophagectomies, 8 foci of high grade dysplasia (HGD) were found in 4 esophagectomies, 4 foci of carcinoma-in-situ (CIS) were found in 2 esophagectomies, and 11 foci of invasive cancer were found in 5 esophagectomies. Because of the small number of foci and the fact that CIS was adjacent, e.g., in the same section, to the invasive cancer, the expression results from LGD and HGD were combined into a DYS category and those from CIS and invasive SCC were combined into a cancer category. RT-PCR analysis identified CTNNB1 splice variants, 16A and 16B, and successfully amplified RT-PCR products for MYC and WAF1 in every histologic category. Mean expression values for all normal, dysplasia, and cancer foci are shown in Table 1.

The geometric mean RNA expression of each CTNNB1 product varies with histologic severity between Nml, DYS, and CA (Table 1). As can be seen in the normal tissue splice variant 16A was about ten times as abundant as 16B. The mean value for 16A was lower in DYS than Nml, but higher in CA than DYS. The mean value for 16B was higher in DYS than Nml, but lower in CA than DYS. In addition, compared to histologically normal appearing epithelium, total CTNNB1 (16A+16B) mRNA expression in DYS was 51% lower. The reduction in total CTNNB1 between N and DYS resulted from a nearly 70% decrease of the more abundant splice variant 16A and a 162% increase of the less abundant variant 16B. Consequently, there was a significant reduction in the 16A/16B mRNA expression ratio ($p=0.014$) between N and DYS. Downstream markers MYC and WAF1 also varied across the spectrum of histologic lesions, with changes in MYC values paralleling those in 16B and WAF values changing parallel to 16A. Quantification of downstream markers of transcription showed over a 78% higher MYC mRNA expression in DYS than Nml epithelium, where as WAF1 was 52% lower in DYS than Nml ($p=0.026$). As a consequence of these differences in directionality, the MYC/WAF1 expression ratio was also reduced ($p=0.001$).

The data shown here in Example 2 demonstrate that two CTNNB1 transcripts, differing by the presence (16A) or absence (16B) of a 159-bp non-coding segment of exon 16, in histologically normal appearing esophageal epithelium, squamous dysplasia and invasive ESCC. In contrast to prior immunohistochemical analysis which showed an increase in protein, we found a reduction in the total CTNNB1 mRNA expression in dysplastic epithelium. The results also show that the ratio for the CTNNB1 splice variants is significantly reduced with histologic progression from normal to dysplastic epithelium. In the context of the protein findings and in the absence of exon 3 mutations, these results suggest that there may be preferential processing and an increase in the minor mRNA 16B isoform with progression from a normal histology to DYS. Although this study was not designed to determine the mechanism behind such a change, possible explanations include, without wishing to be bound by any scientific theories, an increase in transcription efficiency, mRNA stability, or a decrease in nuclear export of the 16B isoform. Such mechanisms are consistent with studies showing that 3' untranslated regions can contain several regulatory elements governing the spatial and temporal expression of mRNA (Kuersten Nature 2003, Hurlstone EMBO 2002, Cok Journal of Biological Chemistry 2001).

The mean CTNNB1 mRNA expression alterations are accompanied by increased mean cMYC and decreased mean WAF1 mRNA expression that synergistically favor an increase in cell transcription (Bitzer Anticancer Research 2003). This is consistent with the fact that MYC and WAF represent TCF target genes and are part of a potential malignant transformation cascade involving CTNNB1 in the gastrointestinal tract (Hurlstone EMBO 2002, Van de Wetering Cell 2002). This is also consistent with the finding that the β-catenin/TCF-4 complex controls proliferation versus differentiation in healthy and malignant intestinal epithelial cells by affecting MYC and WAF1 activity which control G1 arrest and differentiation (Van de Wetering Cell 2002). These genes seem also to be involved in the neoplastic progression of esophageal tumors as well as sites outside of the gastrointestinal tract (Wang L D World J Gastroenterol 1998, Sarbia M AJP 1999, Polakis Genes and Development 2000, Tselepis Gut 2003).

The pattern of the changes in CTNNB1, MYC and WAF1 expression with progression from DYS to CA trending toward the levels found in histologically normal epithelium suggests that these genes may play a more significant role in the earlier stages of neoplastic progression, from normal to DYS and/or the malignant potential of the cellular population comprising cancerous lesions is more heterogeneous than that found in preneolastic lesions.

These specific changes, as used herein, are effective early detection and disease prevention strategies.

Example 3

Statistical Analysis

Gene expression values were transformed using natural log. Due to small numbers, LGD and HGD were analyzed together as DYS, and CIS and invasive squamous cell carcinomas were analyzed together as CA. The percent change in expression from normal to DYS and CA was estimated using linear mixed models including a random intercept for participant. Grade was described with two indicator variables that were treated as fixed effects. Due to the range of samples per specimen additional models with a fixed effect for the number of samples per specimen were examined to test for effect modification between the number of samples and histology (results not shown). All tests of statistical significance were two-sided. Statistical analyses were performed using S-PLUS (S-PLUS version 6.1 for Windows. Seattle (Wash.): Insightful Corporation; 2002).

Example 4

Figure 6:
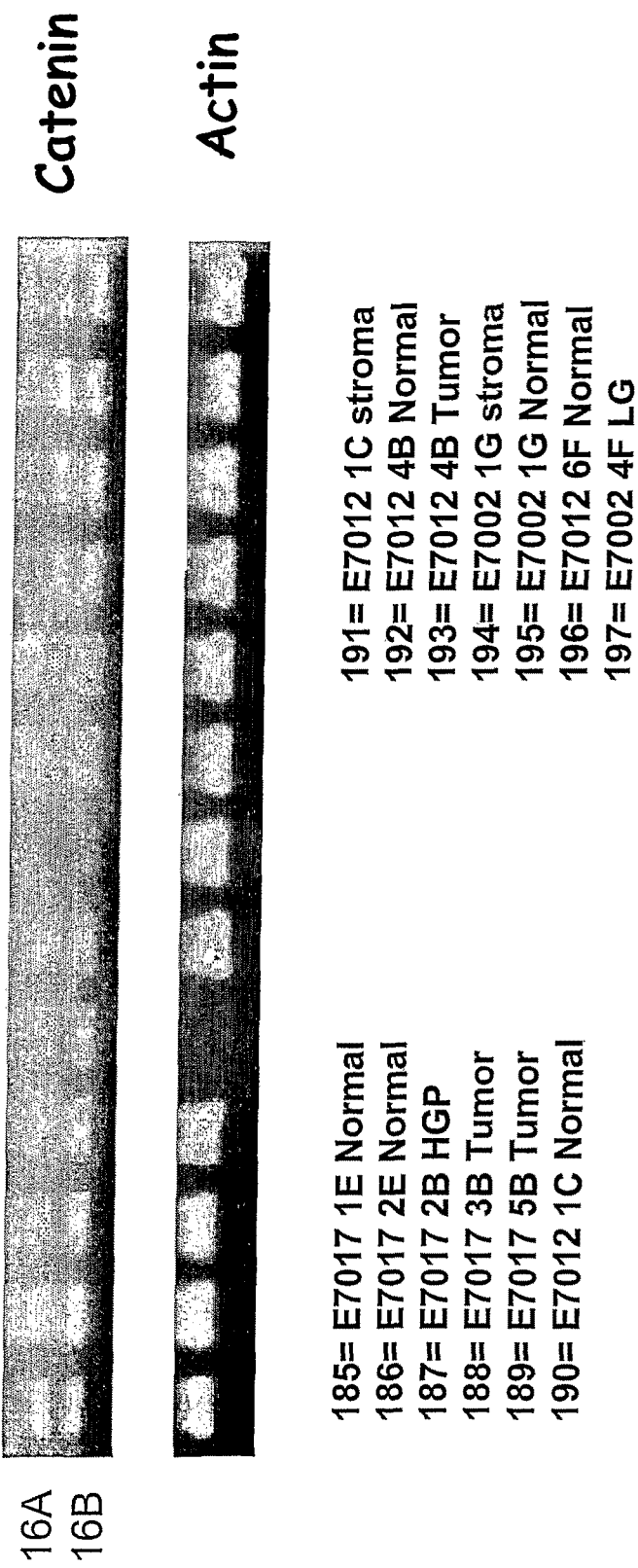
FIG. 6 depicts the results of an RT-PCR amplification of laser capture microdissected (LCM) esophageal samples. RNA was isolated from tissue foci using a standard Trizol extraction protocol in the presence of yeast carrier tRNA. Approximately 25% of the resultant RNA was used from each LCM sample for the synthesis of cDNA. Using the Thermoscript RT-PCR Synthesis (Invitrogen) System, oligo dT and random hexamer primers were employed to synthesize cDNA following the manufacturer's protocol. Primers specific for the 16A (Forward 5' to 3' gtt atc aag agg act aaa tac ca (SEQ ID NO.: 8), Reverse 5' to 3' gac aat aca gct aaa tga tga t (SEQ ID NO.: 9) and 16B isotypes (Forward 5' to 3' gtt atc aag agg act aaa tac ca (SEQ ID NO.: 10), Reverse 5' to 3' gta ttg tta ctc cta aag gat ga (SEQ ID NO.: 11)) of CTNNB1 and Beta-Actin were used to amplify specific products. The uppermost bands of the gel figure represents the 16A and 16B isotypes, respectively, for beta-catenin each numbered case tested. The beta-actin control band is present in the window beneath beta-catenin FIG. 7 A-G graphically depict the results of the analysis of splice variants from normal, dysplastic, and cancer-in-situ and invasive lesions.

Referring to FIG. 6, these results are derived from the six fully blocked frozen esophagectomy specimens, with an average of 7 (range 3 to 15) foci per specimen representing the histologic spectrum of neoplastic progression from normal to invasive squamous cell carcinoma that were selected for RT-PCR analysis. From these resections, a total of 11 foci of histologically normal (Nml) epithelium were found in 4 esophagectomies, 11 foci of low grade dysplasia (LGD) were found in 6 esophagectomies, 8 foci of high grade dysplasia (HGD) were found in 4 esophagectomies, 4 foci of carcinoma-in-situ (CIS) were found in 2 esophagectomies, and 11 foci of invasive cancer were found in 5 esophagectomies. Because of the small number of foci and the fact that CIS was adjacent, e.g., in the same section, to the invasive cancer, the expression results from LGD and HGD were combined into a DYS category and those from CIS and invasive SCC were combined into a Cancer category. RT-PCR analysis identified CTNNB1 splice variants, 16A and 16B, and successfully amplified RT-PCR products for MYC and WAF1 in every histologic category.: Real Time RT-PCR analysis: Resection specimens from six patients were fully submitted in histology cassettes and stored at −70 degrees C. until Real Time RT-PCR analysis of CTNNB1, MYC and WAF1.

Serial 5-micron frozen sections were cut from each histology cassette and representative foci of normal (N=11), low grade dysplasia (N=11), high grade dysplasia (N=8), carcinoma in-situ (N=4), and invasive squamous cell carcinoma (N=11) from the six fully submitted esophageal resections were chosen based on histologic review by a pathologist (MR) of corresponding hematoxylin and eosin stained slides using accepted histologic criteria. RNA was isolated from laser capture microdissected these tissue foci using a standard Trizol extraction protocol in the presence of yeast carrier tRNA. Approximately 25% of the resultant RNA was used from each LCM sample for the synthesis of cDNA. Using the Thermoscript RT-PCR Synthesis (Invitrogen) System, oligo dT and random hexamer primers were employed to synthesize cDNA following the manufacturer's protocol. Primers specific for the 16A and 16B isotypes of CTNNB1, c-MYC, p21 (WAF1), GAPDH, 18s rRNA and Beta-Actin (Table 1) were used to amplify specific products either with SYBR green (50 cycles—Real Time RT-PCR) or without SYBR green (35 cycles conventional gel-based RT-PCR).

Unless specified, all reaction conditions were conducted in Platinum Supermix (Invitrogen) using standard PCR conditions including a reannealing temperature of 55° C. For standardizing Real Time PCR product concentrations, purified inserts of the appropriate products were used in serial dilutions and then plotted on a log-scale to calculate starting quantity (threshold starting cycle). All samples were normalized to housekeeping controls (Beta-actin) prior to calculating levels of gene expression. This study was approved by the Institutional Review Boards for the Shanxi Cancer Hospital, Shanxi, China, and the National Cancer Institute, Bethesda, Md., United States. Mean expression values for all normal, dysplasia, and cancer foci are shown in Table 1.

TABLE 2

Geometric mean of mRNA expression for participants with normal histology and % change ($\Delta$) of expression from normal to dysplasia and cancer[†]

|  | Normal, mean (95% C.I.)* | Dysplasia, $\Delta$ (95% C.I.)* | Cancer, $\Delta$ (95% C.I.)* |
|---|---|---|---|
| Beta-Catenin 16A | 2.2 ($10^{-8}$) (0.6 to 8.0) | −69% (−91% to 9.4%) | −22% (−79% to 197%) |
| Beta-Catenin 16B | 1.7 ($10^{-9}$) (0.4 to 6.9) | 162% (−32% to 913%) | 94% (−55% to 735%) |
| 16A + 16B | 3.4 ($10^{-8}$) (1.2 to 9.4) | −51% (−81% to 29%) | −17% (−70% to 135%) |
| 16A/16B | 13.1 (2.5 to 68) | −88%** (−97% to −40%) | −61% (−93% to 108%) |
| Myc | 8.5 ($10^{-9}$) (4.6 to 16) | 78% (−9.3% to 248%) | 45% (−29% to 196%) |
| Waf | 9.6 ($10^{-7}$) (5.1 to 18.0) | −52%** (−74% to −11%) | 34% (−31% to 161%) |
| Myc/Waf | 0.008 (0.003 to 0.02) | 283%** (84% to 701%) | 31% (−42% to 194%) |

*Estimates of percent change are from linear mixed models, including participant as a random effect and grade as a fixed effect treated as two indicator variables.
**Compared to normal tissue, the percent change of mRNA expression in dysplasia is significantly different for Waf (p = 0.026) and the 16A/16B (p = 0.014) and Myc/Waf (p = 0.001) ratios.
[†]6 participants with a total of 43 observations for 16A + 16B and 16A/16B, 44 observations for 16A, 16B, Waf, and ratio Myc/Waf; and 45 observations for Myc.

Example 5

Small inhibitor RNA (siRNA) molecules were designed to target the 16B and 16A+16B isoforms of CTNNB1. The use of the inhibitors demonstrates that the expression of downstream markers of proliferation, cMYC and WAF1 were modulated, thus illustrating the use of CTNNB1 splice-variant related therapeutics in treating CTNNB1 related cancers.

This data represents first silencing of CTNNB1 (16A and 16B) or the 16A variant in the 293-H kidney cells. siRNA constructs were designed to either the amino terminal region of the CTNNB1 (CTNNB1-1 and -2) or sequences residing within the alternate splice sequence 16A (16A-1 and -2). The siRNAs were used at a concentration of 50 nM. The 293-H cells were harvested after 48 hours and the expression levels determined by RT-PCR of extracted RNA. Negative controls were assayed without siRNA silencing constructs to determine control expression levels for both CTNNB1 alternate splice sequences, e.g., 16A and 16B, in addition to MYC, WAF1 and Actin using the same Real Time RT-PCR assay.

Silencing with either CTNNB1 construct (16A/16B-1 or 16A/16B-2) results in greater than a 95% reduction in expression, in comparison to non-silenced expression, of the 16A and 16B alternate splice sequences (Table 2). Expression of downstream markers of transcription, MYC and WAF1, were also reduced by the siRNA CTNNB1 constructs. In addition, 16A directed siRNA constructs (16A-1 and 16A-2) showed an even more striking reduction in both CTNNB1 splice variants, with the absence of splice variant specificity for the two 16A constructs having yet to be determined. Furthermore, and, silencing with either 16A-1 or 16A-2 produces an increase in WAF1 expression and a concomitant decrease in MYC expression resulting in a reduction of the MYC to WAF1 ratio (ratio=<1) with respect to the non-silencing experiment (ratio=192).

These results are further depicted in the bar graph (FIG. 1) where the x-axis reflects relative copy numbers for each of the genes assayed (e.g. 15/16A, 15/16B, MYC and WAF1). Thus, non-silencing (top panel) shows high levels of MYC with respect to WAF1 and CTNNB1, with comparable levels of 16A and B splice variants. Silencing with 16A-1 or 16A-2 significantly reduces the amount of 16A, and to a lesser degree 16B, and reduces MYC expression while slightly increasing WAF1 expression. Treating with CTNNB1-1 (16A/16B-2) or CTNNB1-2 (16A/16B-1) reduces both 16A and 16B splice variants and decreases MYC expression more than WAF1 expression. Each response to siRNA CTNNB1 directed modulation is consistent with reduced transcription and with reduced neoplastic potential. Results were obtained with 8 repeating wells (silencing) or 16 repeating wells (non-silencing) and results from each individual well were averaged to determine the final real-time expression levels.

TABLE 3

Quantitative Real Time RT-PCR of CTNNB1 with and without siRNA to alternate splice sequence16A*

| | 16A/16B-1 | 16A/16B-2 | 16A-1 | 16A-2 | non-silencing |
|---|---|---|---|---|---|
| 15/16A | 1.68E–14 | 1.08E–13 | 2.40E–12 | 1.89E–12 | 1.54E–08 |
| 15/16B | 4.48E–12 | 4.45E–12 | 9.34E–11 | 1.39E–10 | 7.21E–09 |
| MYC | 8.57E–11 | 1.18E–09 | 6.22E–09 | 7.24E–09 | 2.79E–06 |
| WAF1 | 5.38E–12 | 1.79E–09 | 5.74E–08 | 4.87E–08 | 1.45E–08 |
| Actin | | | | | 3.98E–07 |
| Ratios | | | | | |
| 16A/16B | 0.00375 | 0.024 | 0.026 | 0.0136 | 2.13E+00 |
| MYC/WAF1 | 15.9 | 0.66 | 0.108 | 0.149 | 1.92E+02 |

*All expression levels normalized to the internal control Actin

All references cited herein, whether in print, electronic, computer readable storage media or other form, are incorporated herein by reference in their entirety, including abstracts, articles, journals, publications, texts, treatises, technical data sheets, internet web sites, databases, patents, patent applications, and patent publications.

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting the presence or absence of a β-catenin gene (CTNNB1) related esophageal cancer in a subject, comprising:
   (a) obtaining a subject sample;
   (b) determining the proportion of 16A transcript to 16B transcript in a cell or cells from the subject sample;
   (c) comparing the proportion of 16A transcript to 16B transcript to a standard proportion,
   (d) identifying a decrease in a 16A transcript level relative to a 16B transcript level in the subject sample; and
   (e) identifying the subject as having a CTNNB1 related esophageal cancer; or performing said steps (a) to (c) and
   (f) not identifying a decrease in a 16A transcript level relative to a 16B transcript level in the subject sample; and
   (g) identifying the subject as not having a CTNNB1 related esophageal cancer.

2. The method of claim 1, wherein the subject is anywhere along the progression from normal to neoplastic.

3. The method of claim 1, wherein the esophageal cancer in the subject is an esophageal preneoplastic squamous epithelium, an esophageal squamous dysplasia, an esophageal squamous cell carcinoma in-situ, an invasive esophageal squamous cell carcinoma, or any histological or cytological stage in-between.

4. The method of claim 1, wherein the β-catenin gene (CTNNB1) related esophageal cancer is one or more of esophageal squamous cell carcinoma (ESCC), esophageal adenocarcinoma, esophageal dysplasia, and esophageal metaplasia.

5. The method of claim 1, wherein the proportions are determined by PCR methods.

6. A method of diagnosing if a subject may have a β-catenin gene (CTNNB1) related esophageal cancer, comprising:
   (a) determining the proportion of 16A transcript to 16B transcript in a cell or cells obtained from the subject;
   (b) comparing the proportion of 16A transcript to 16B transcript to a standard proportion;
   (c) identifying a decrease in a 16A transcript level relative to a 16B transcript level in the cell or cells;
   (d) identifying the cancer as a CTNNB1 related cancer; or performing said steps (a) to (b) and
   (e) not identifying a decrease in a 16A transcript level relative to a 16B transcript level in the cell or cells;
   (f) identifying the cancer as not likely a CTNNB1 related cancer.

7. The method of claim 6, wherein the esophageal cancer is one or more of esophageal squamous cell carcinoma (ESCC), esophageal adenocarcinoma, esophageal dysplasia, and esophageal metaplasia.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tatgggaaca attgaagtaa a                                                    21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cagaaagtgc ctgacacact a                                                    21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcgggatgt tcacaaccga a                                                    21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgggtaggg taaatcagta a                                                    21

<210> SEQ ID NO 5
```

<211> LENGTH: 3697
<212> TYPE: DNA
<213> ORGANISM: Homo sapiens

<400> SEQUENCE: 5

| | | | | | |
|---|---|---|---|---|---|
| cccacgcgtc | cgggcagcag | cgttggcccg | gccccgggag | cggagagcga | ggggaggcgg | 60 |
| agacggagga | aggtctgagg | agcagcttca | gtccccgccg | agccgccacc | gcaggtcgag | 120 |
| gacggtcgga | ctcccgcggc | gggaggagcc | tgttccctg | agggtatttg | aagtatacca | 180 |
| tacaactgtt | ttgaaaatcc | agcgtggaca | atggctactc | aagctgattt | gatggagttg | 240 |
| gacatggcca | tggaaccaga | cagaaaagcg | gctgttagtc | actggcagca | acagtcttac | 300 |
| ctggactctg | gaatccattc | tggtgccact | accacagctc | cttctctgag | tggtaaaggc | 360 |
| aatcctgagg | aagaggatgt | ggatacctcc | caagtcctgt | atgagtggga | cagggatt | 420 |
| tctcagtcct | tcactcaaga | acaagtagct | gatattgatg | acagtatgc | aatgactcga | 480 |
| gctcagaggt | acgagctgc | tatgttccct | gagacattag | atgagggcat | gcagatccca | 540 |
| tctacacagt | ttgatgctgc | tcatcccact | aatgtccagc | gtttggctga | accatcacag | 600 |
| atgctgaaac | atgcagttgt | aaacttgatt | aactatcaag | atgatgcaga | acttgccaca | 660 |
| cgtgcaatcc | ctgaactgac | aaaactgcta | aatgacgagg | accaggtggt | ggttaataag | 720 |
| gctgcagtta | tggtccatca | gctttctaaa | aaggaagctt | ccagacacgc | tatcatgcgt | 780 |
| tctcctcaga | tggtgtctgc | tattgtacgt | accatgcaga | atacaaatga | tgtagaaaca | 840 |
| gctcgttgta | ccgctgggac | cttgcataac | cttttcccatc | atcgtgaggg | cttactggcc | 900 |
| atctttaagt | ctggaggcat | tcctgccctg | gtgaaaatgc | ttggttcacc | agtggattct | 960 |
| gtgttgtttt | atgccattac | aactctccac | aacctttat | tacatcaaga | aggagctaaa | 1020 |
| atggcagtgc | gtttagctgg | tgggctgcag | aaaatggttg | ccttgctcaa | caaaacaaat | 1080 |
| gttaaattct | tggctattac | gacagactgc | cttcaaattt | tagcttatgg | caaccaagaa | 1140 |
| agcaagctca | tcatactggc | tagtggtgga | ccccaagctt | tagtaaatat | aatgaggacc | 1200 |
| tatacttacg | aaaaactact | gtggaccaca | agcagagtgc | tgaaggtgct | atctgtctgc | 1260 |
| tctagtaata | agccggctat | tgtagaagct | ggtggaatgc | aagctttagg | acttcacctg | 1320 |
| acagatccaa | gtcaacgtct | tgttcagaac | tgtctttgga | ctctcaggaa | tctttcagat | 1380 |
| gctgcaacta | acaggaagg | gatggaaggt | ctccttggga | ctcttgttca | gcttctgggt | 1440 |
| tcagatgata | taaatgtggt | cacctgtgca | gctggaattc | tttctaacct | cacttgcaat | 1500 |
| aattataaga | acaagatgat | ggtctgccaa | gtgggtggta | tagaggctct | tgtgcgtact | 1560 |
| gtccttcggg | ctggtgacag | ggaagacatc | actgagcctg | ccatctgtgc | tcttcgtcat | 1620 |
| ctgaccagcc | gacaccaaga | agcagagatg | gcccagaatg | cagttcgcct | tcactatgga | 1680 |
| ctaccagttg | tggttaagct | cttacaccca | ccatcccact | ggcctctgat | aaaggctact | 1740 |
| gttggattga | ttcgaaatct | tgcccttttgt | cccgcaaatc | atgcaccttt | gcgtgagcag | 1800 |
| ggtgccattc | cacgactagt | tcagttgctt | gttcgtgcac | atcaggatac | ccagcgccgt | 1860 |
| acgtccatgg | gtgggacaca | gcagcaattt | gtggagggg | tccgcatgga | agaaatagtt | 1920 |
| gaaggttgta | ccggagccct | tcacatccta | gctcgggatg | ttcacaaccg | aattgttatc | 1980 |
| agaggactaa | ataccattcc | attgtttgtg | cagctgcttt | attctcccat | tgaaaacatc | 2040 |
| caaagagtag | ctgcagggt | cctctgtgaa | cttgctcagg | acaggaagc | tgcagaagct | 2100 |
| attgaagctg | agggagccac | agctcctctg | acagagttac | ttcactctag | gaatgaaggt | 2160 |
| gtggcgacat | atgcagctgc | tgttttgttc | cgaatgtctg | aggacaagcc | acaagattac | 2220 |

```
aagaaacggc tttcagttga gctgaccagc tctctcttca gaacagagcc aatggcttgg    2280
aatgagactg ctgatcttgg acttgatatt ggtgcccagg gagaacccct tggatatcgc    2340
caggatgatc ctagctatcg ttcttttcac tctggtggat atggccagga tgccttgggt    2400
atggacccca tgatggaaca tgagatgggt ggccaccacc ctggtgctga ctatccagtt    2460
gatgggctgc cagatctggg gcatgcccag gacctcatgg atgggctgcc tccaggtgac    2520
agcaatcagc tggcctggtt tgatactgac ctgtaaatca tcctttaggt aagaagtttt    2580
aaaaagccag tttgggtaaa atacttttac tctgcctaca gaacttcaga aagacttggt    2640 tggtaggtg ggagtggttt aggctatttg taaatctgcc acaaaaacag gtatatactt    2700
tgaaaggaga tgtcttggaa cattggaatg ttctcagatt tctggttgtt atgtgatcat    2760
gtgtggaagt tattaacttt aatgtttttt gccacagctt ttgcaactta atactcaaat    2820
gagtaacatt tgctgtttta aacattaata gcagcctttc tctctttata cagctgtatt    2880
gtctgaactt gcattgtgat tggcctgtag agttgctgag agggctcgag gggtgggctg    2940
gtatctcaga aagtgcctga cacactaacc aagctgagtt tcctatggga acaattgaag    3000
taaacttttt gttctggtcc tttttggtcg aggagtaaca atacaaatgg attttgggag    3060
tgactcaaga agtgaagaat gcacaagaat ggatcacaag atggaattta gcaaaccta    3120 gccttgcttg ttaaaatttt ttttttttttt tttaagaat atctgtaatg gtactgactt    3180
tgcttgcttt gaagtagctc tttttttttt tttttttttt ttttttttgc agtaactgtt    3240
ttttaagtct ctcgtagtgt taagttatag tgaatactgc tacagcaatt tctaattttt    3300
aagaattgag taatggtgta gaacactaat taattcataa tcactctaat taattgtaat    3360
ctgaataaag tgtaacaatt gtgtagcctt tttgtataaa atagacaaat agaaaatggt    3420
ccaattagtt tcctttttaa tatgcttaaa ataagcaggt ggatctattt catgtttttg    3480
atcaaaaact atttgggata tgtatgggta gggtaaatca gtaagaggtg ttatttggaa    3540
ccttgttttg gacagtttac cagttgcctt ttatcccaaa gttgttgtaa cctgctgtga    3600
tacgatgctt caagagaaaa tgcggttata aaaatggtt cagaattaaa cttttaattc    3660
attcaaaaaa aaaaaaaaaa aaaaaaaaaa aaaaaaa                            3697

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctaatgctaa tactgtttcg t                                             21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tactcttacc agctacttgt tctt                                          24

<210> SEQ ID NO 8
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 8
gttatcaaga ggactaaata cca                                          23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gacaatacag ctaaatgatg at                                           22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttatcaaga ggactaaata cca                                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtattgttac tcctaaagga tga                                          23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agccacaaga ttacaagaaa c                                            21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggctagggt ttgctaaatt c                                            21

<210> SEQ ID NO 14
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 14 gccctggtg ctccatga                                                      18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
accctcttgg cagcaggata                                                   20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acagcagagg aagaccatgt g                                                 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggcttcctc ttggagaaga t                                                 21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcaagaacga aagtcggagg                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggacatctaa gggcatcaca                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 20
ccacactgtg cccatctacg                                                 20

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagcggaacc gctcattgcc aatgg                                           25

<210> SEQ ID NO 22
<211> LENGTH: 781
<212> TYPE: PRT
<213> ORGANISM: Homo sapiens

<400> SEQUENCE: 22

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Ala Pro Ser Leu Ser Gly
            35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

-continued

```
Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720
```

```
Ser Gly Gly Tyr Gly Gln Asp Ala Leu Gly Met Asp Pro Met Met Glu
            725                 730                 735

His Glu Met Gly Gly His His Pro Gly Ala Asp Tyr Pro Val Asp Gly
            740             745                 750

Leu Pro Asp Leu Gly His Ala Gln Asp Leu Met Asp Gly Leu Pro Pro
        755             760                 765

Gly Asp Ser Asn Gln Leu Ala Trp Phe Asp Thr Asp Leu
    770             775                 780
```